(12) United States Patent
Metsger et al.

(10) Patent No.: US 8,252,805 B2
(45) Date of Patent: Aug. 28, 2012

(54) FORMS OF LAPATINIB DITOSYLATE AND PROCESSES FOR PREPARATION THEREOF

(75) Inventors: Leonid Metsger, Beer-Sheva (IL); Ariel Mittelman, Elad (IL); Slavik Yurkovski, Kiryat-Gat (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 407 days.

(21) Appl. No.: 12/437,498

(22) Filed: May 7, 2009

(65) Prior Publication Data

US 2009/0281315 A1 Nov. 12, 2009

Related U.S. Application Data

(60) Provisional application No. 61/126,862, filed on May 7, 2008, provisional application No. 61/054,261, filed on May 19, 2008, provisional application No. 61/130,240, filed on May 28, 2008, provisional application No. 61/073,219, filed on Jun. 17, 2008, provisional application No. 61/081,570, filed on Jul. 17, 2008, provisional application No. 61/082,754, filed on Jul. 22, 2008, provisional application No. 61/088,918, filed on Aug. 14, 2008, provisional application No. 61/091,633, filed on Aug. 25, 2008, provisional application No. 61/092,635, filed on Aug. 28, 2008, provisional application No. 61/102,068, filed on Oct. 2, 2008, provisional application No. 61/109,382, filed on Oct. 29, 2008, provisional application No. 61/200,665, filed on Dec. 1, 2008, provisional application No. 61/153,442, filed on Feb. 18, 2009, provisional application No. 61/163,720, filed on Mar. 26, 2009, provisional application No. 61/053,465, filed on May 15, 2008, provisional application No. 61/054,935, filed on May 21, 2008, provisional application No. 61/091,992, filed on Aug. 26, 2008.

(51) Int. Cl.
*A01N 43/54* (2006.01)
*A61K 31/517* (2006.01)
*C07D 239/72* (2006.01)

(52) U.S. Cl. ............ 514/266.1; 544/276; 544/283
(58) Field of Classification Search ............ 514/266.1; 544/278, 283, 276
See application file for complete search history.

(56) References Cited

U.S. PATENT DOCUMENTS

| | | |
|---|---|---|
| 6,391,874 B1 | 5/2002 | Cockerill et al. |
| 6,713,485 B2 | 3/2004 | Carter et al. |
| 6,727,256 B1 | 4/2004 | Carter et al. |
| 6,828,320 B2 | 12/2004 | Cockerill et al. |
| 6,933,299 B1 | 8/2005 | Cockerill et al. |
| 7,141,576 B2 | 11/2006 | Lackey et al. |
| 7,157,466 B2 | 1/2007 | McClure et al. |
| 2003/0220354 A1 | 11/2003 | McClure et al. |
| 2005/0119288 A1 | 6/2005 | Bhattacharya et al. |
| 2007/0015775 A1 | 1/2007 | Carter et al. |
| 2008/0051422 A1 | 2/2008 | Tung |
| 2008/0058519 A1 | 3/2008 | Osterhout et al. |

FOREIGN PATENT DOCUMENTS

| | | |
|---|---|---|
| EP | 2 060565 | 5/2009 |
| WO | WO 96/09294 | 3/1996 |
| WO | WO 98/02437 | 1/1998 |
| WO | WO 99/35146 | 7/1999 |
| WO | WO 01/04111 | 1/2001 |
| WO | WO 02/02552 | 1/2002 |
| WO | WO 02/02552 A1 * | 1/2002 |
| WO | WO 02/056912 | 7/2002 |
| WO | WO 03/086467 | 10/2003 |
| WO | WO 2005/046678 | 5/2005 |
| WO | WO 2005/105094 | 11/2005 |
| WO | WO 2005/120504 | 12/2005 |
| WO | WO 2005/120512 | 12/2005 |
| WO | WO 2006/026313 | 3/2006 |
| WO | WO 2006/066267 | 6/2006 |
| WO | WO 2006/113649 | 10/2006 |
| WO | WO 2007/143483 | 12/2007 |
| WO | WO 2008/024439 | 2/2008 |
| WO | WO 2008/033749 | 3/2008 |
| WO | WO 2008/154469 | 12/2008 |
| WO | WO 2009/079541 | 6/2009 |
| WO | WO 2009/079547 | 6/2009 |

OTHER PUBLICATIONS

Ambike et al., "Spray-Dried Amorphous Solid Dispersions of Simvastatin, a Low Tg Drug: In Vitro and in Vivo Evaluations", Pharmaceutical Research, Kluwer Academic Publishers Plenum Publishers, NE, Jun. 1, 2005, vol. 22, No. 6, p. 990-998.

Boyd et al., "Lapatinib", Drugs of the Future, 30(12):1225-1239 (2005).

Kim et al.; "Lapatinib Ditosylate," *IDrugs*, Current Drugs Ltd., GB, vol. 6, No. 9, pp. 886-893 (2003).

Korich et al., "A Facile, One-Pot Procedure for Forming Diarylimines from itroarenes and Benzadehydes", Synlett, 16: 2602 (2007).

McClure et al., "A Practical One-Pot Synthesis of 5-aryl-2-furaldehydes", Synthesis, 11:1681-1682 (2001).

Perry's Chemical Engineer's Handbook, 1984, 6th ed., pp. 20-54 to 20-57.

Remington: The Science and Practice of Pharmacy, 19th Ed., vol. 2, p. 1627-1628 (1995).

(Continued)

*Primary Examiner* — Paul V. Ward

(74) *Attorney, Agent, or Firm* — Kenyon & Kenyon LLP

(57) ABSTRACT

The present invention provides novel polymorphs of lapatinib ditosylate, processes for preparing them, and pharmaceutical compositions comprising one or more of these polymorphs.

7 Claims, 23 Drawing Sheets

OTHER PUBLICATIONS

Petrov et al., "Optimization and SAR for dual ErB-1/Erb-2 tyrosine kinase inhibition in the 6-furanylquinazoline series", *Bioorganic & Medicinal Chemistry Letters*, 16: 4686-4691 (2006).

International Search Report of Application PCT/US2009/043197, dated Feb. 2, 2010.

Caira, "Crystalline Polymorphism of Organic Compounds", Topics in Current Chemistry, 1998, vol. 198, p. 163-208.

Anderton, "A Valuable Technique for Polymorph Screening", European Pharmaceutical Review, 2004, vol. 9, No. 2, p. 68-74.

Sacchetti, "Determining the Relative Physical Stability of Anhydrous and Hydrous Crystal Forms of GW2016", International Journal of Pharmaceutics, 2004, vol. 273, p. 195-202.

Bai et al., "Determination of Lapatinib (GW572016) in Human Plasma by Liquid Chromatography Electrospray Tandem Mass Spectrometry (LC-ESI-MS/MS)", Journal of Chromatography, 2006, vol. 831, p. 169-175.

Invitation to Pay Additional Fees, dated Oct. 19, 2009, from corresponding International Patent Application PCT/US2009/043197.

* cited by examiner

PXRD of Form XI of lapatinib ditosylate produced by grinding with ethanol (top) or IPA (bottom) of Form I of lapatinib ditosylate.

FORMS OF LAPATINIB DITOSYLATE AND PROCESSES FOR PREPARATION THEREOF

RELATED APPLICATIONS

This application claims the benefit under 35 U.S.C. §119 (e) of U.S. Provisional Application Nos. 61/126,862, filed May 7, 2008; 61/054,261, filed May 19, 2008; 61/130,240, filed May 28, 2008; 61/073,219, filed Jun. 17, 2008; 61/081,570, filed Jul. 17, 2008; 61/082,754, filed Jul. 22, 2008; 61/088,918, filed Aug. 14, 2008; 61/091,633, filed Aug. 25, 2008; 61/092,635, filed Aug. 28, 2008; 61/102,068, filed Oct. 2, 2008; 61/109,382, filed Oct. 29, 2008; 61/200,665, filed Dec. 1, 2008; 61/153,442, filed Feb. 18, 2009; 61/163,720 filed, Mar. 26, 2009; 61/053,465, filed May 15, 2008; 61/054,935, filed May 21, 2008; and 61/091,992, filed Aug. 26, 2008, each of which is incorporated herein by reference in its entirety.

FIELD OF THE INVENTION

The invention encompasses new polymorphs of lapatinib ditosylate, and processes for preparation thereof.

BACKGROUND OF THE INVENTION

Lapatinib ditosylate, N-[3-chloro-4-[(3-fluorophenyl)methoxy]phenyl]-6-[5-[(2-methylsulfonylethylamino)methyl]-2-furyl]quinazolin-4-amine ditosylate, has the following chemical structure:

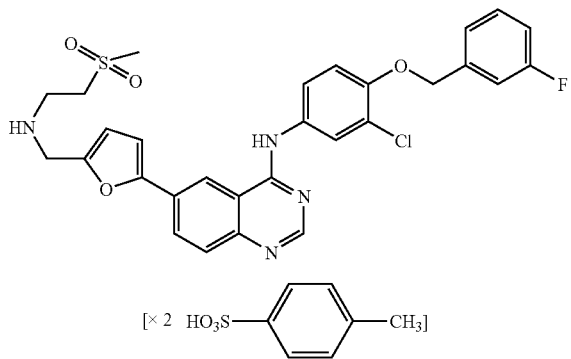

Lapatinib ditosylate is currently marketed in the United States under the tradename TYKERB® by GlaxoSmithKline. It was approved by the FDA as a drug for use in patients with advanced metastatic breast cancer.

Lapatinib ditosylate is described in PCT publications WO1999/035146, WO2002/002552, WO2005/046678, WO2006/113649, WO1998/002437, WO2001/004111, WO1996/009294, WO2002/056912, WO2005/105094, WO2005/120504, WO2005/120512, WO2006/026313, and WO2006/066267.

Two polymorphs of lapatinib ditosylate, anhydrous and monohydrate forms are described in U.S. Pat. No. 7,157,466 (WO 2002/002552).

The present invention relates to the solid state physical properties of lapatinib ditosylate. These properties can be influenced by controlling the conditions under which lapatinib ditosylate is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular polymorphic form of a substance. These conformational and orientation factors in turn result in particular intramolecular interactions such that different polymorphic forms may give rise to distinct spectroscopic properties that may be detectable by powder X-ray diffraction, solid state $^{13}$C NMR spectrometry and infrared spectrometry. A particular polymorphic form may also give rise to thermal behavior different from that of the amorphous material or another polymorphic form. Thermal behavior is measured in the laboratory by such techniques as capillary melting point, thermogravimetric analysis (TGA) and differential scanning calorimetry (DSC) and can be used to distinguish some polymorphic forms from others.

The discovery of new polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. There is a need in the art for additional polymorphic forms of lapatinib ditosylate.

SUMMARY OF THE INVENTION

The present invention encompasses novel solid crystalline forms of lapatinib ditosylate referred to herein as Form I, Form II, Form III, Form IV, Form V, Form VI, Form VII, Form VIII, Form IX, Form XI, Form XII, Form XIII, Form XIV, Form XV, Form XVI, Form XVII, Form XVIII, and Form XIX; processes for preparing thereof, and pharmaceutical compositions containing one or more of these forms.

DETAILED DESCRIPTION OF THE INVENTION

Figure 1:
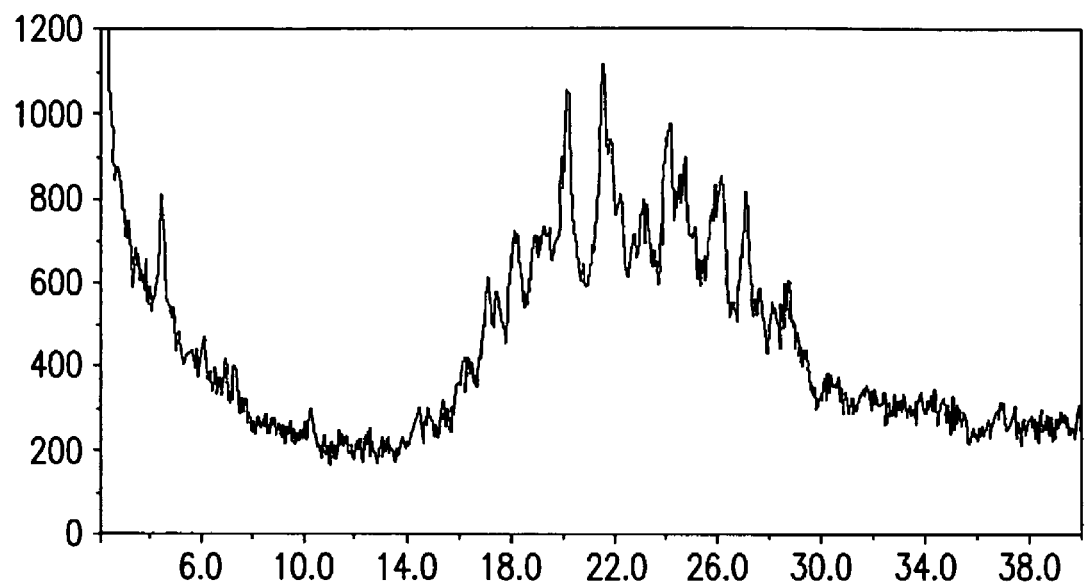
FIG. 1 shows a powder X-ray diffraction pattern for Form I of lapatinib ditosylate, as obtained in Example 1.

As used herein, the term "lapatinib ditosylate" includes any solid state composition of lapatinib base and p-toluenesulfonic acid. For example: a salt, a co-crystal, or a solid mixture of base and acid.

As used herein, the terms "slurry", or "suspension" refer to a mixture of suspended solids in liquid (solvent). Typically, the solvent is used in an amount that does not result in the full dissolution of the substance.

As used herein, the term "neat condition" refers to a reaction which is carried out without the presence of a solvent.

As used herein, a "wet crystalline form" refers to a polymorph that was not dried using any conventional techniques.

As used herein, a "dry crystalline form" refers to a polymorph that was dried using any conventional techniques.

As used herein, drying is carried out at elevated temperature under reduced pressure. Preferably, the crystalline form is dried at about 40° C. to about 90° C., more preferably, between about 60° C. and about 70° C., and, most preferably, about 60° C. Preferably the drying is carried out under reduced pressure (for example less than 1 atmosphere, more preferably, about 10 mbar to about 100 mbar, more preferably, about 10 mbar to about 25 mbar). Preferably the drying takes place over a period of about 8 hours to about 36 hours, more preferably, about 10 hours to about 24 hours, and, most preferably, about 12 hours.

As used herein, the term "overnight" refers to a period of about 12 hours to about 24 hours.

As used herein, an antisolvent is a liquid that when added to a solution of a solute in a solvent, induces, enhances or facilitates precipitation of the solute. Precipitation of lapatinib ditosylate (also referred to as "lapatinib-DTS"), for example, may be induced by an antisolvent when addition of the antisolvent causes lapatinib ditosylate to precipitate from the solution, or to precipitate more rapidly, or to precipitate to a greater extent than lapatinib ditosylate would precipitate out of the solvent without the antisolvent. As used herein, the term volume ("V") refers to ml per gram. For example, 30 V means 30 ml solvent per one gram of compound.

As used herein, the term "room temperature" refers to a temperature of about 20° C. to about 30° C.

As used herein, lapatinib base Form X refers to a crystalline lapatinib base characterized by a data selected from the group consisting of: a PXRD pattern having peaks at about 20.0, 21.3, 24.0, 24.6 and 27.0±0.2 degrees 2-theta; and a PXRD pattern having peaks at about 6.8, 11.4, 16.0, 16.9, 18.0, 20.0, 21.3, 24.0, 24.6 and 27.0±0.2 degrees 2-theta. Lapatinib base Form X can be obtained using any method known in the art, for example, by forming a slurry of lapatinib ditosylate and acetonitrile; and adding an inorganic base to obtain Lapatinib base Form X.

Unless stated otherwise, wherever p-toluenesulfonic acid is used, at least two equivalents of the acid are added, more preferably about 2-4 equivalents, even more preferably about 2-3 equivalents, and most preferably about 2-2.5 equivalents are added.

The present invention relates to novel solid crystalline forms of lapatinib ditosylate referred to herein as Form I, Form II, Form III, Form IV, Form V, Form VI, Form VII, Form VIII, Form IX, Form XI, Form XII, Form XIII, Form XIV, Form XVI, Form XVII, Form XVIII, and Form XIX.

In one embodiment, the invention encompasses Form I of lapatinib ditosylate characterized by data selected from the group consisting of a PXRD pattern having peaks at about 4.4, 20.0, and 21.5±0.2 degrees 2-theta, and at least two peaks selected from the group consisting of 10.2, 18.1, 24.0, 24.6, 26.0 and 27.1±0.2 degrees 2-theta; a solid state $^{13}$C NMR spectrum with signals at about 110.2, 127.1 and 137.4±0.2 ppm; and a solid-state $^{13}$C NMR spectrum having chemical shifts differences between the signal exhibiting the lowest chemical shift and another in the chemical shift range of 100 to 180 ppm of about 0.0, 16.9 and 27.2±0.1 ppm, wherein the signal exhibiting the lowest chemical shift in the chemical shift area of 100 to 180 ppm is typically at about 110.2±1 ppm.

Preferably, the peaks at about 4.8 or at about 6.6±0.2 degrees two-theta are absent wherein the analysis is done at a scan rate slow enough, according to the common knowledge of the skilled in the art. The scan rate used may vary from instrument to instrument, and sample preparation.

Figure 2:
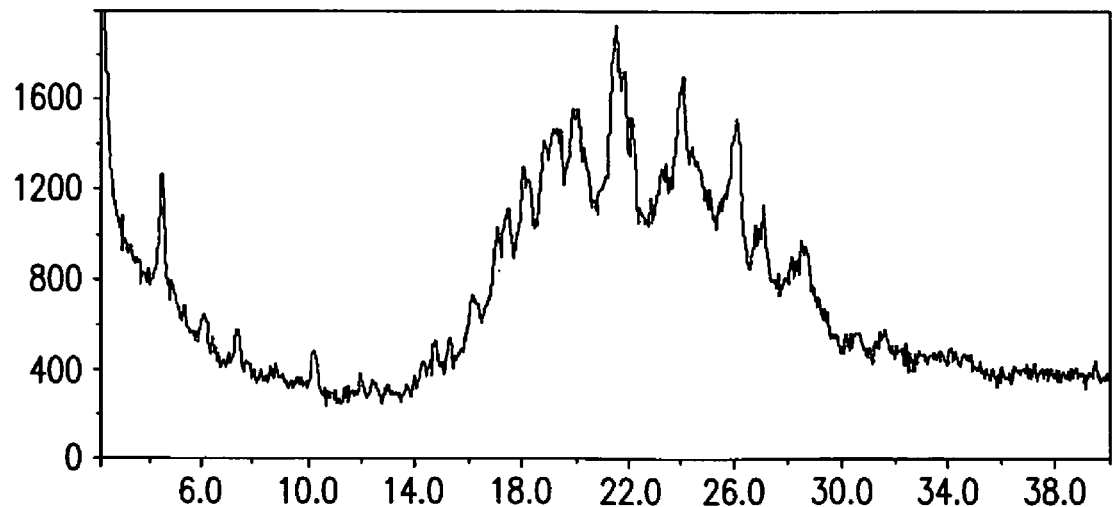
FIG. 2 shows a powder X-ray diffraction pattern for Form I of lapatinib ditosylate, as obtained in Example 9.

In another embodiment, the present invention encompasses Form I of lapatinib ditosylate as characterized by a PXRD pattern illustrated in FIGS. 1-2.

Figure 33:
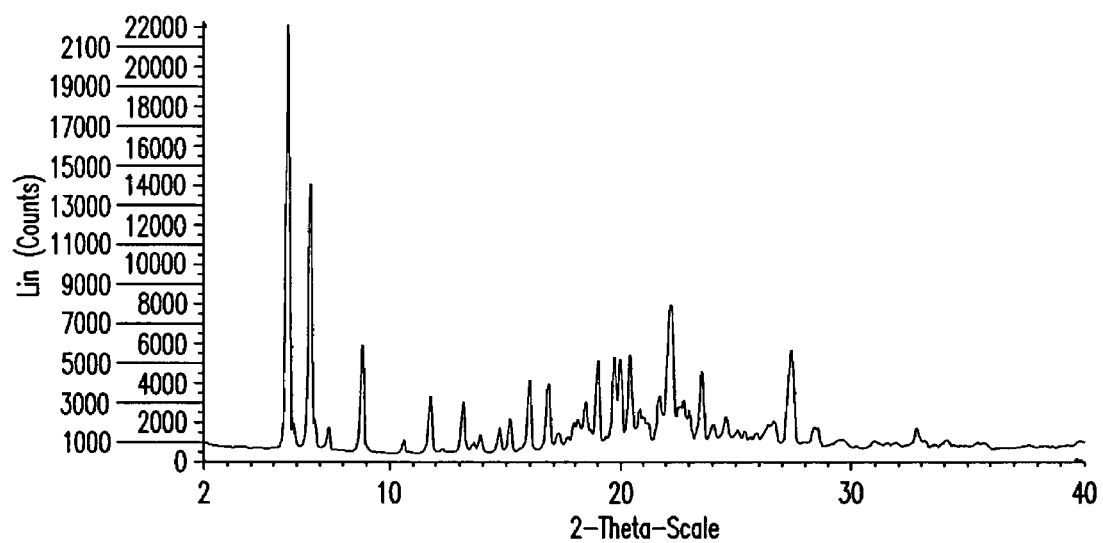
FIG. 33 shows a powder X-ray diffraction pattern for Form XVIII of lapatinib ditosylate.
Figure 34:
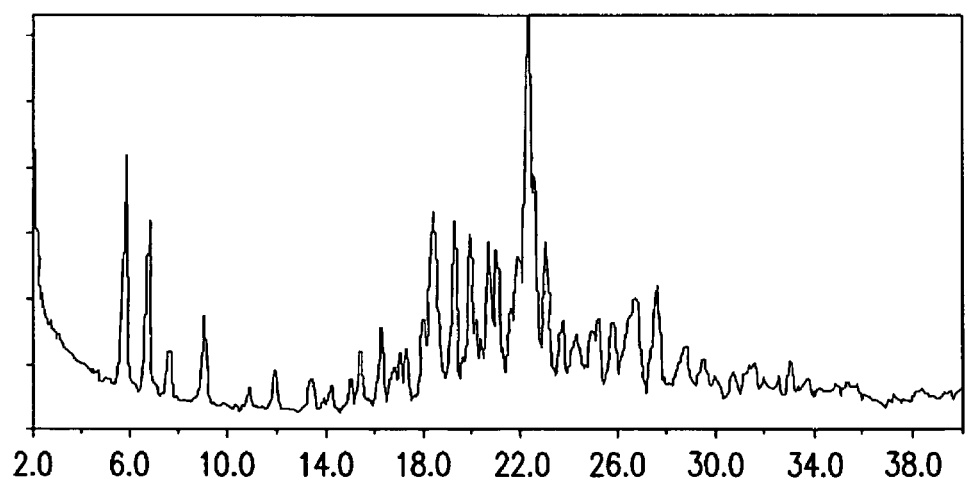
FIG. 34 shows a powder X-ray diffraction pattern for Form XVIII of lapatinib ditosylate, as obtained in Example 92.

In another embodiment, the present invention encompasses Form I of lapatinib ditosylate as characterized by a solid state $^{13}$C NMR spectrum illustrated in FIGS. 33 and 34.

In another embodiment, the invention encompasses crystalline Form II of lapatinib ditosylate characterized by a PXRD pattern having peaks at about 8.5, 12.8, and 15.1±0.2 degrees 2-theta, and at least two peaks selected from the group consisting of 4.3, 19.4, 19.8, 21.5, and 30.5±0.2 degrees 2-theta.

Figure 3:
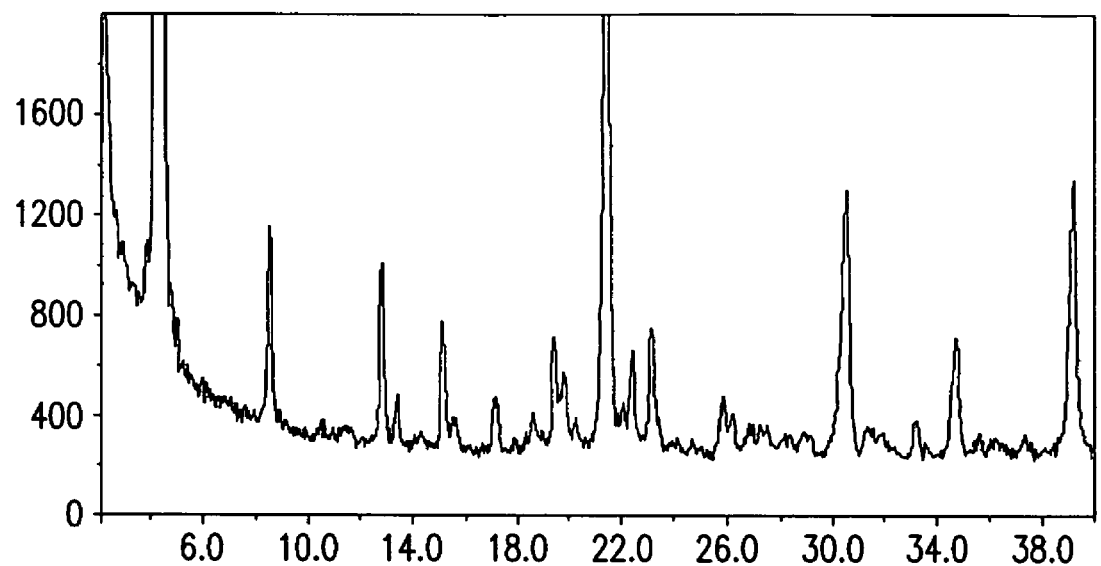
FIG. 3 shows a powder X-ray diffraction pattern for Form II of lapatinib ditosylate, as obtained in Example 3, experiment no. 6.
Figure 4:
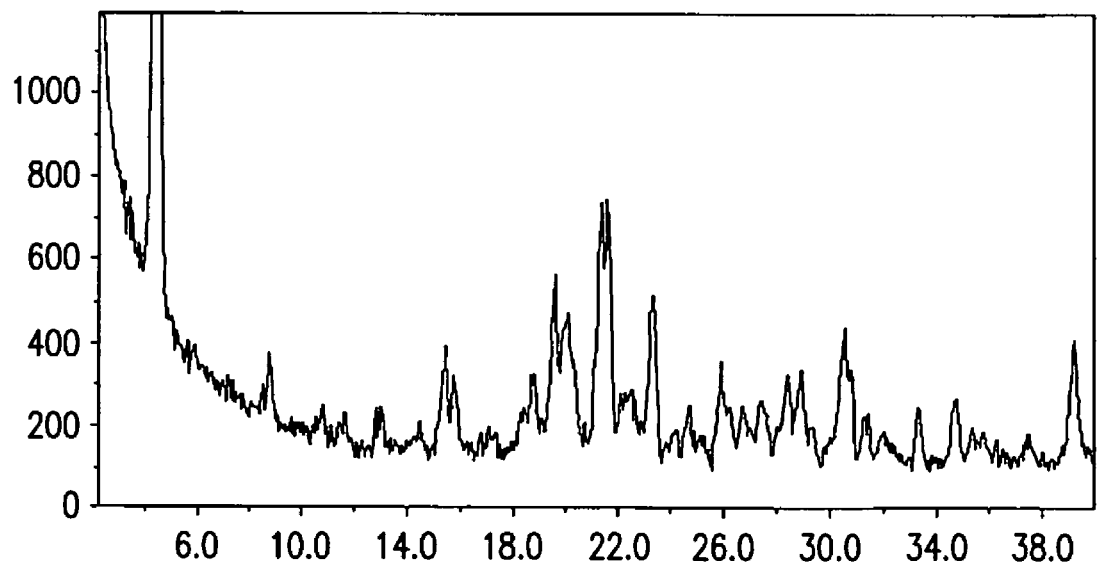
FIG. 4 shows a powder X-ray diffraction pattern for Form II of lapatinib ditosylate, as obtained in Example 3, experiment no. 5.

In another embodiment, the present invention encompasses crystalline Form II of lapatinib ditosylate as characterized by PXRD patterns illustrated in FIGS. 3-4.

In another embodiment, the invention encompasses crystalline Form III of lapatinib ditosylate characterized by a PXRD pattern having peaks at about 4.7, 14.2, and 15.3±0.2 degrees 2-theta, and at least two peaks selected from the group consisting of 3.8, 7.6, 19.2, 19.7, and 23.1±0.2 degrees 2-theta.

Figure 5:
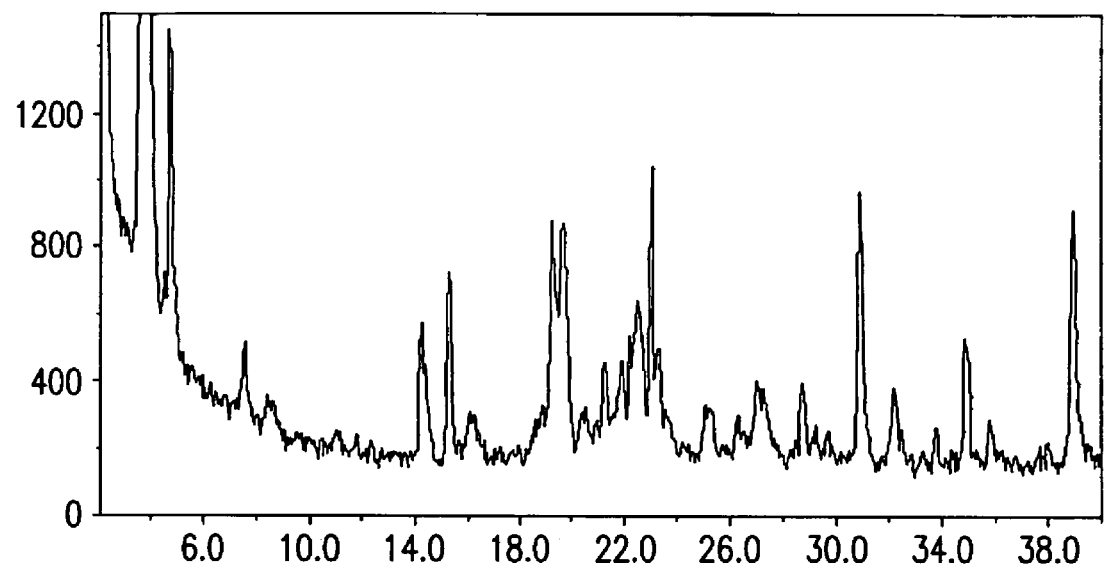
FIG. 5 shows a powder X-ray diffraction pattern for Form III of lapatinib ditosylate.

In another embodiment, the present invention encompasses crystalline Form III of lapatinib ditosylate as characterized by a PXRD pattern illustrated in FIG. 5.

In another embodiment, the invention encompasses crystalline Form IV of lapatinib ditosylate characterized by a PXRD pattern having peaks at about 8.6, 11.7, and 13.4±0.2 degrees 2-theta, and at least two peaks selected from the group consisting of 4.6, 15.3, 15.6, 18.9, 19.5, 22.4, and 23.5±0.2 degrees 2-theta.

Figure 6:
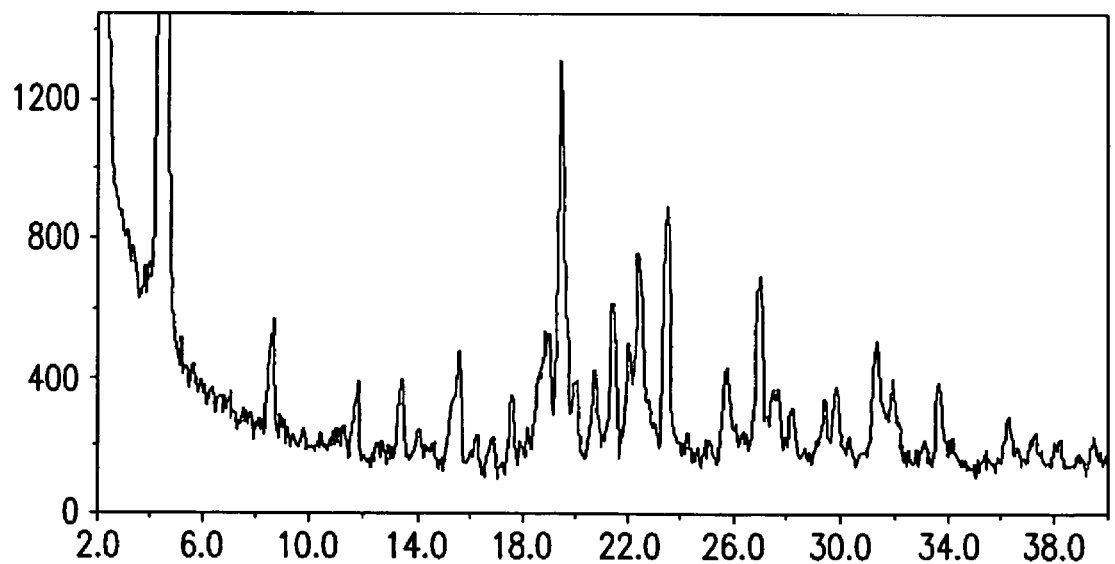
FIG. 6 shows a powder X-ray diffraction pattern for Form IV of lapatinib ditosylate.

In another embodiment, the present invention encompasses crystalline Form IV of lapatinib ditosylate as characterized by a PXRD pattern illustrated in FIG. 6.

In another embodiment, the invention encompasses crystalline Form V of lapatinib ditosylate characterized by data selected from the group consisting of: a PXRD pattern having peaks at about 12.8, 15.5, and 18.5±0.2 degrees 2-theta, and at least two peaks selected from the group consisting of 4.2, 8.7, 20.5, 21.4, 26.4 and 30.0±0.2 degrees 2-theta; a PXRD pattern having peaks at about 4.3, 5.7, 6.5, 8.6 and 16.6±0.2 degrees 2-theta; and a PXRD pattern having peaks at about 4.3, 5.7, 6.5, 8.6, 15.6, 16.6, 18.5, 20.2, 21.0 and 23.1+0.2 degrees 2-theta.

Figure 7:
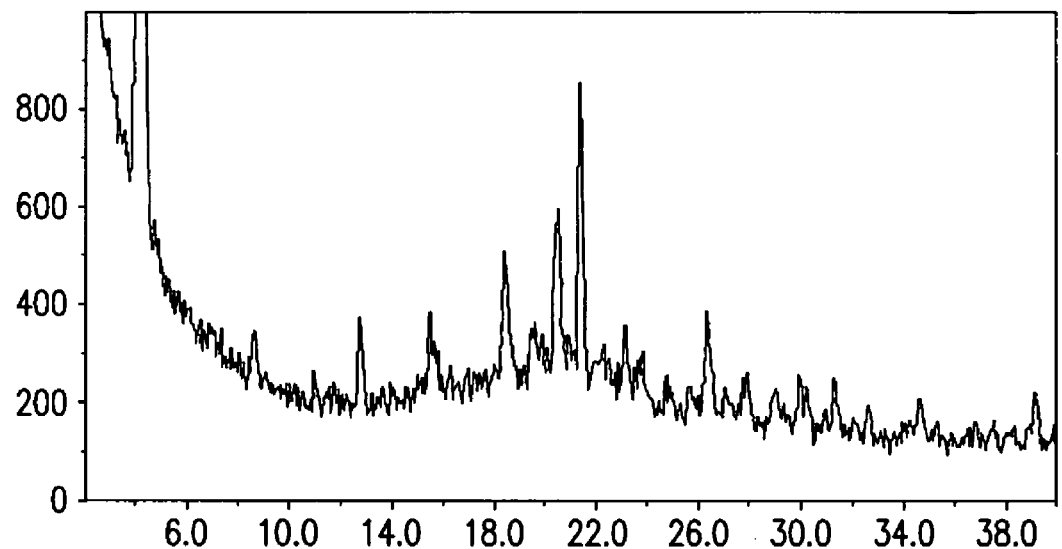
FIG. 7 shows a powder X-ray diffraction pattern for Form V of lapatinib ditosylate.
Figure 8:
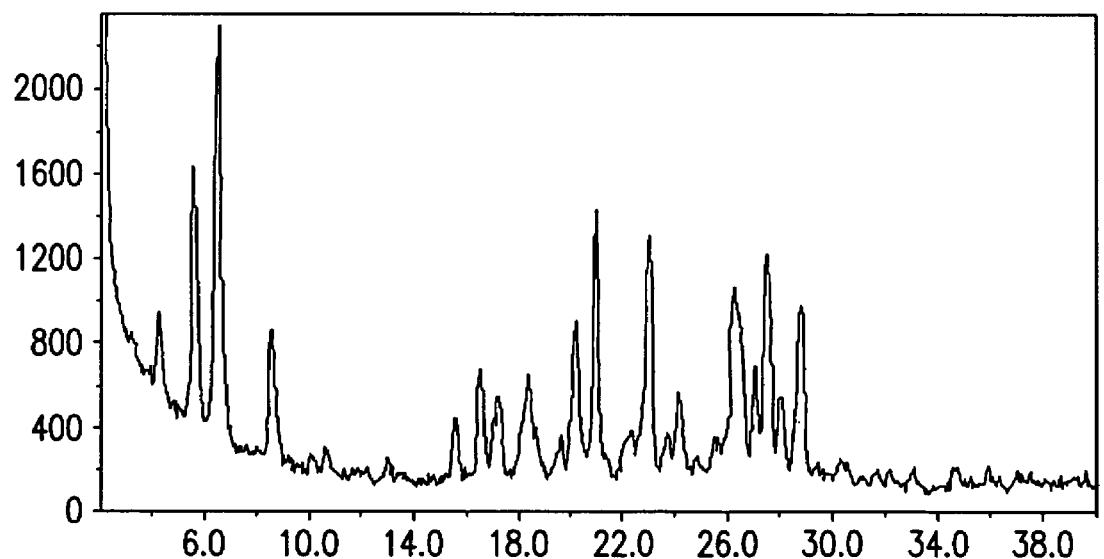
FIG. 8 shows a powder X-ray diffraction pattern for Form VI of lapatinib ditosylate, as obtained in Example 3.
Figure 9:
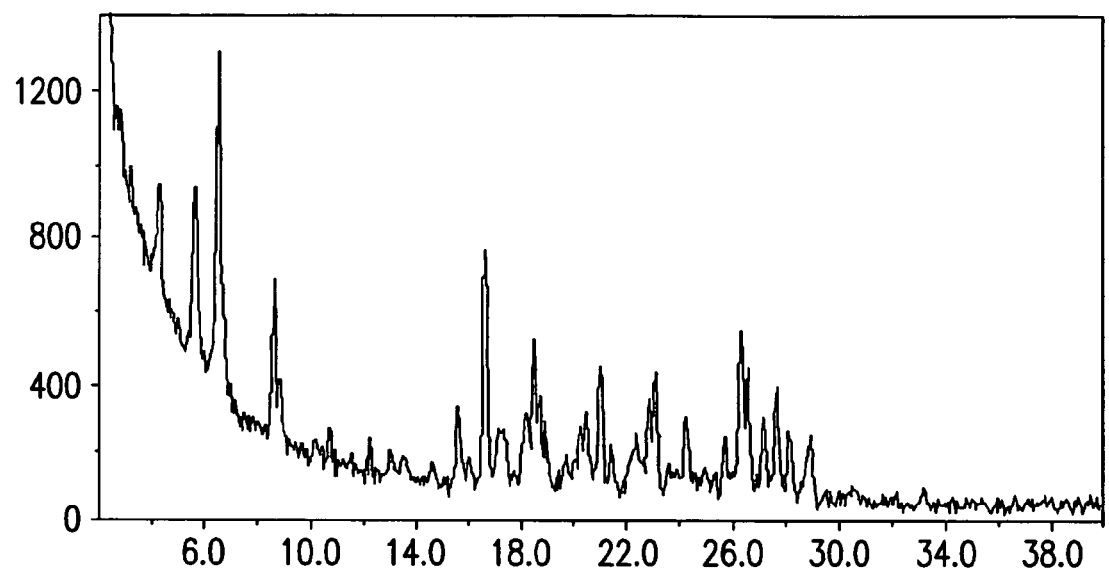
FIG. 9 shows a powder X-ray diffraction pattern for Form VI of lapatinib ditosylate, as obtained in Example 63.
Figure 10:
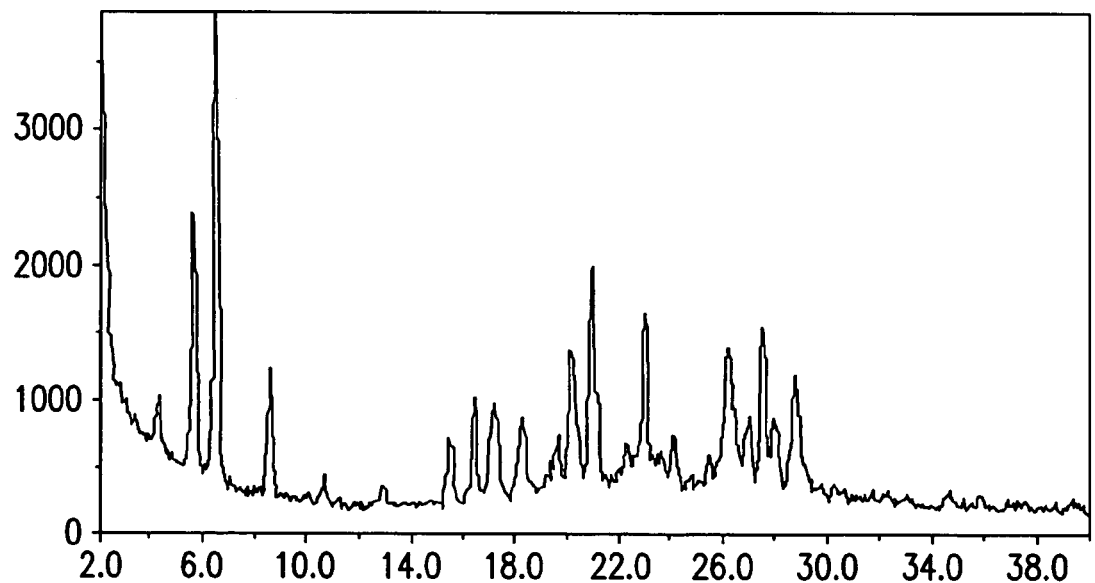
FIG. 10 shows a powder X-ray diffraction pattern for Form VI of lapatinib ditosylate, as obtained in Example 74.

In another embodiment, the present invention encompasses crystalline Form V of lapatinib ditosylate as characterized by a PXRD pattern illustrated in FIG. 7.

In another embodiment, the invention encompasses crystalline Form VI of lapatinib ditosylate characterized by data selected from the group consisting of: a PXRD pattern having peaks at about 5.6, 6.5, and 17.2±0.2 degrees 2-theta, and at least two peaks selected from the group consisting of 4.3, 8.6, 15.5, 16.5, 21.0, 23.1, 27.6 and 28.8±0.2 degrees 2-theta; a PXRD pattern having peaks at about 4.3, 5.7, 6.5, 8.6 and 16.6±0.2 degrees 2-theta; and a PXRD pattern having peaks at about 4.3, 5.7, 6.5, 8.6, 15.6, 16.6, 18.5, 20.2, 21.0 and 23.1±0.2 degrees 2-theta.

In another embodiment, the invention encompasses crystalline Form VI of Lapatinib ditosylate characterized by a PXRD pattern having peaks at about 4.3, 5.7, 6.5, 8.6 and 16.6±0.2 degrees 2-theta.

In another embodiment, the invention encompasses crystalline Form VI of Lapatinib ditosylate characterized by a PXRD pattern having peaks at about 4.3, 5.7, 6.5, 8.6, 15.6, 16.6, 18.5, 20.2, 21.0 and 23.1±0.2 degrees 2-theta.

Figure 11:
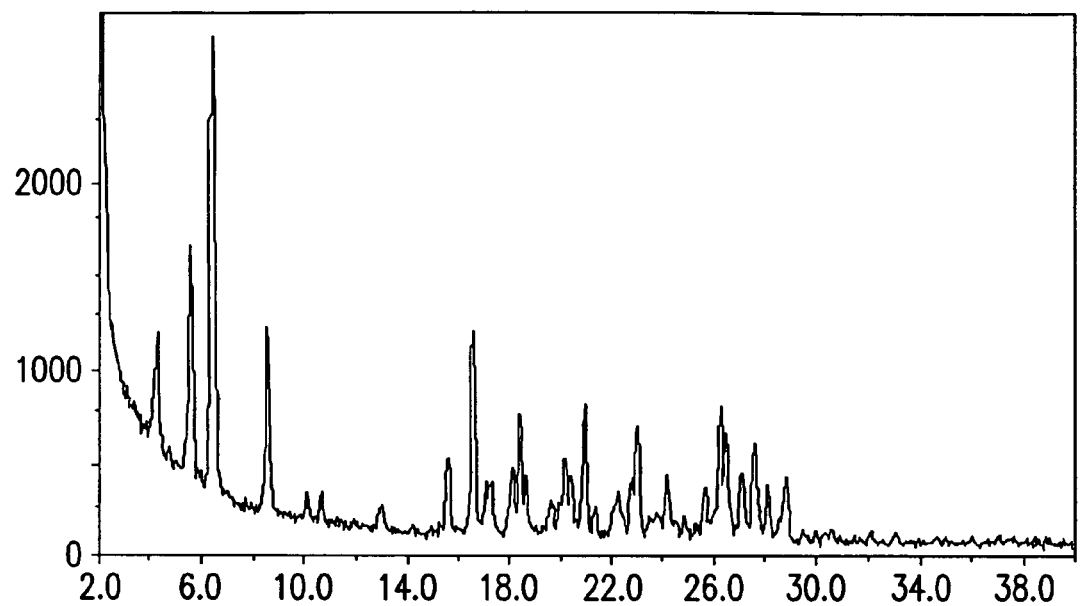
FIG. 11 shows a powder X-ray diffraction pattern for Form VI of lapatinib ditosylate, as obtained in Example 79.

In another embodiment, the present invention encompasses crystalline Form VI of lapatinib ditosylate as characterized by a PXRD pattern illustrated in FIG. 11.

In another embodiment, the invention encompasses crystalline Form VII of lapatinib ditosylate characterized by a PXRD pattern having peaks at about 15.3, 19.0, and 25.2±0.2 degrees 2-theta, and at least two peaks selected from the group consisting of 20.0, 21.5, 23.0, 24.6 and 29.0±0.2 degrees 2-theta.

In another embodiment, the invention encompasses crystalline Form VII of lapatinib ditosylate characterized by a PXRD pattern having peaks at about 15.3, 19.0, and 25.2±0.2 degrees 2-theta, and at least two peaks selected from the group consisting of 20.0, 21.5, 23.0, 24.6 and 29.0±0.2 degrees 2-theta, wherein the crystalline form is substantially free of a peak at about 4.8, or at about 6.6±0.2 degrees two-theta.

Figure 12:
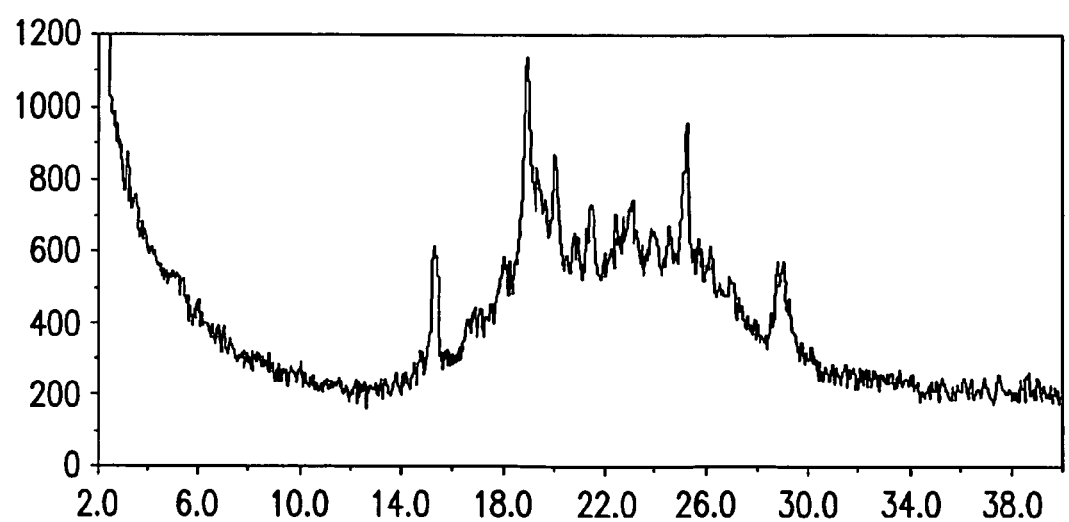
FIG. 12 shows a powder X-ray diffraction pattern for Form VII of lapatinib ditosylate, as obtained in Example 4.
Figure 13:
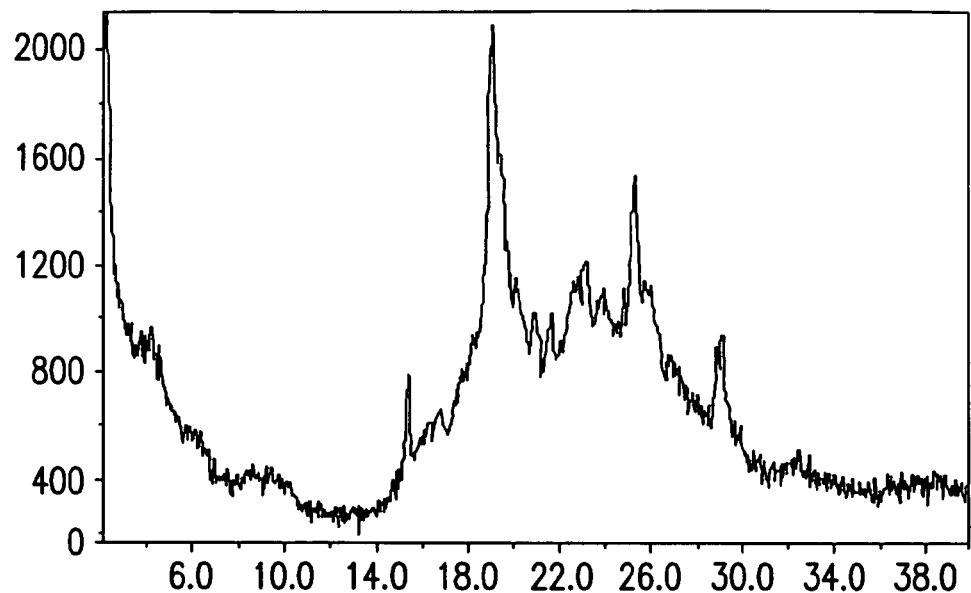
FIG. 13 shows a powder X-ray diffraction pattern for Form VII of lapatinib ditosylate, as obtained in Example 15.

In one embodiment, the present invention encompasses crystalline Form VII of lapatinib ditosylate as characterized by a PXRD pattern illustrated in FIGS. 12-13.

Preferably, the peaks at about 4.8 or at about 6.6±0.2 degrees two-theta are absent wherein the analysis is done at a scan rate slow enough, according to the common knowledge of the skilled in the art. The scan rate used may vary from instrument to instrument, and sample preparation.

In another embodiment, the invention encompasses crystalline Form VIII of lapatinib ditosylate characterized by a PXRD pattern having peaks at about 8.8, 15.1 and 16.1±0.2 degrees 2-theta, and at least two peaks selected from the group consisting of 5.5, 6.5, 16.6, 18.1, 21.9, and 27.1±0.2 degrees 2-theta.

Figure 14:
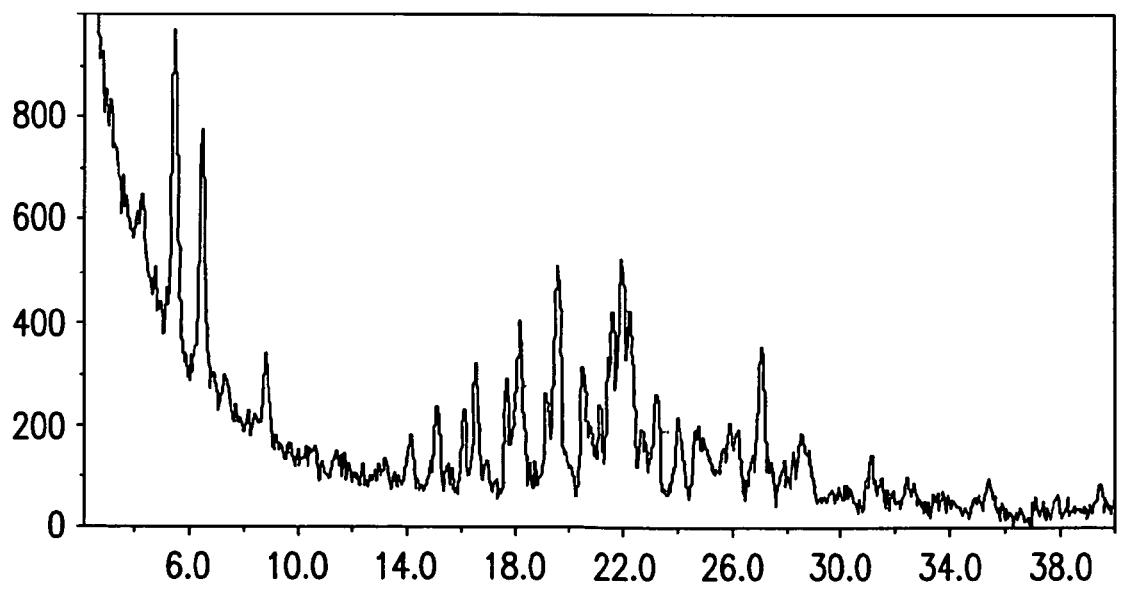
FIG. 14 shows a powder X-ray diffraction pattern for Form VIII of lapatinib ditosylate, as obtained in Example 3.
Figure 15:
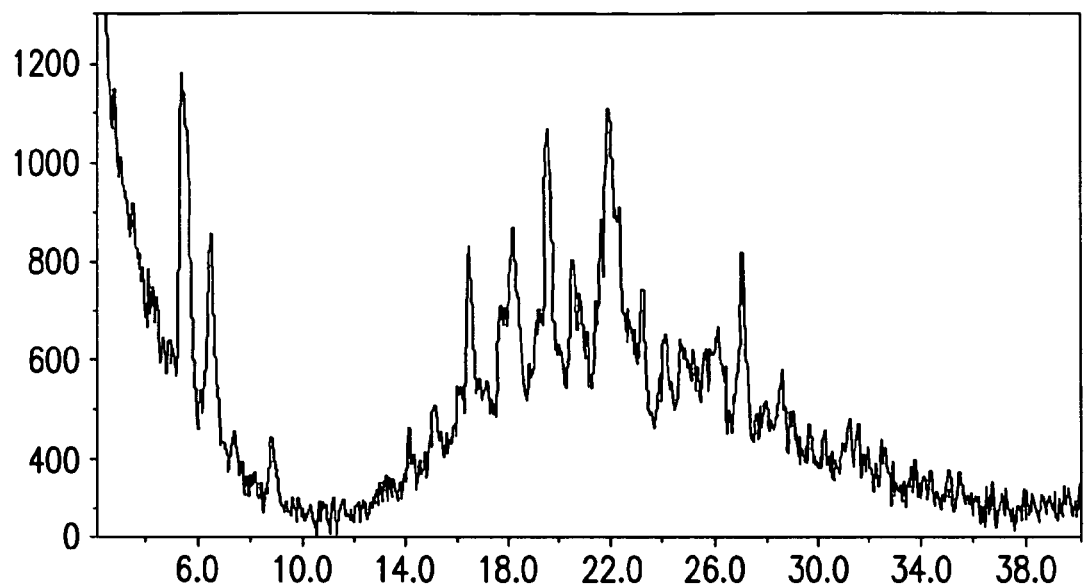
FIG. 15 shows a powder X-ray diffraction pattern for Form VIII of lapatinib ditosylate, as obtained in Example 71.
Figure 16:
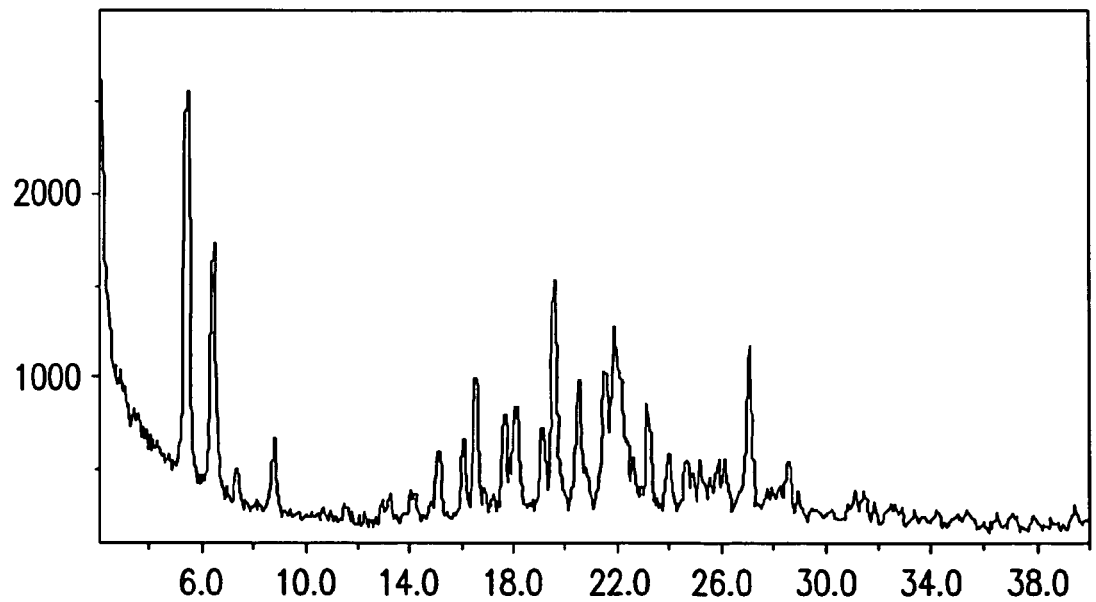
FIG. 16 shows a powder X-ray diffraction pattern for Form VIII of lapatinib ditosylate, as obtained in Example 77.

In another embodiment, the present invention encompasses crystalline Form VIII of lapatinib ditosylate as characterized by a PXRD pattern illustrated in FIG. 14.

In another embodiment, the invention encompasses Form IX of lapatinib ditosylate characterized by a PXRD pattern having peaks at about 4.1, 5.4, and 8.1±0.3 degrees 2-theta, and at least two peaks selected from the group consisting of 16.2, 18.0, 19.7 and 22.7+0.2 degrees 2-theta.

Figure 17:
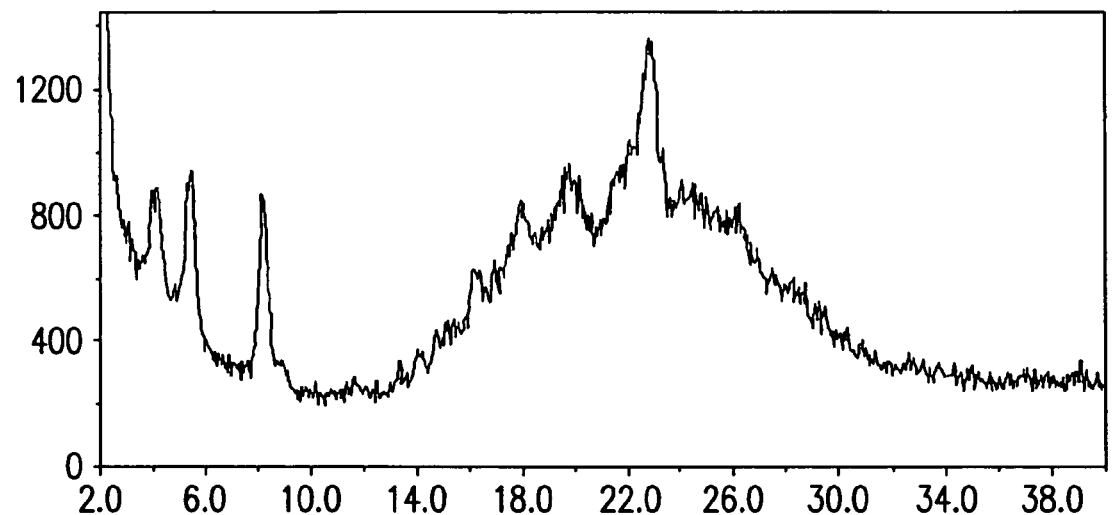
FIG. 17 shows a powder X-ray diffraction pattern for Form IX of lapatinib ditosylate.

In one embodiment, the present invention encompasses Form IX of lapatinib ditosylate as characterized by a PXRD pattern illustrated in FIG. 17.

In another embodiment, the invention encompasses Form XI of lapatinib ditosylate characterized by a PXRD pattern with broad peaks with a maxima at about 4.1 to about 4.3 and a maxima at about 19.0 to about 19.2, and two additional very broad peaks defined by angle ranges of about 21.5 to about 24.5, and about 24.5 to about 27.0 in degrees 2-theta. Preferably, Form XI is substantially amorphous.

Figure 18:
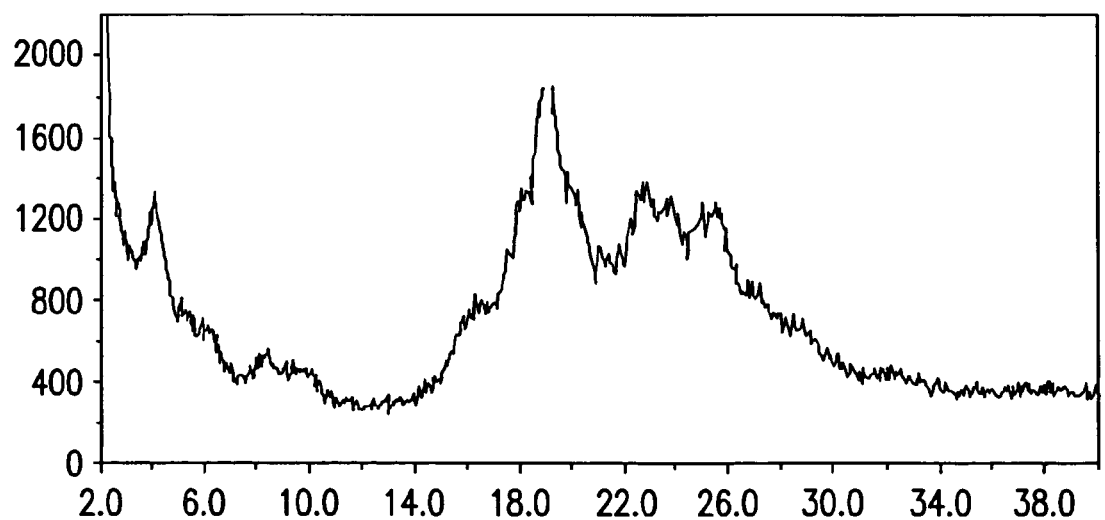
FIG. 18 shows a powder X-ray diffraction pattern for Form XI of lapatinib ditosylate, as obtained in Example 11.
Figure 19:
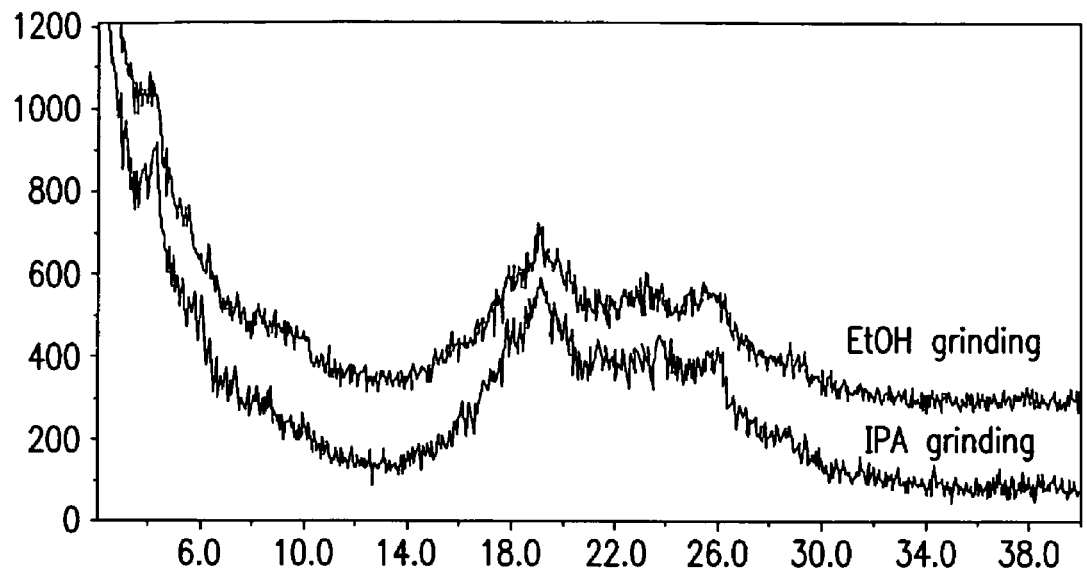
FIG. 19 shows a powder X-ray diffraction pattern for Form XI of lapatinib ditosylate, as obtained in Example 12.
Figure 20:
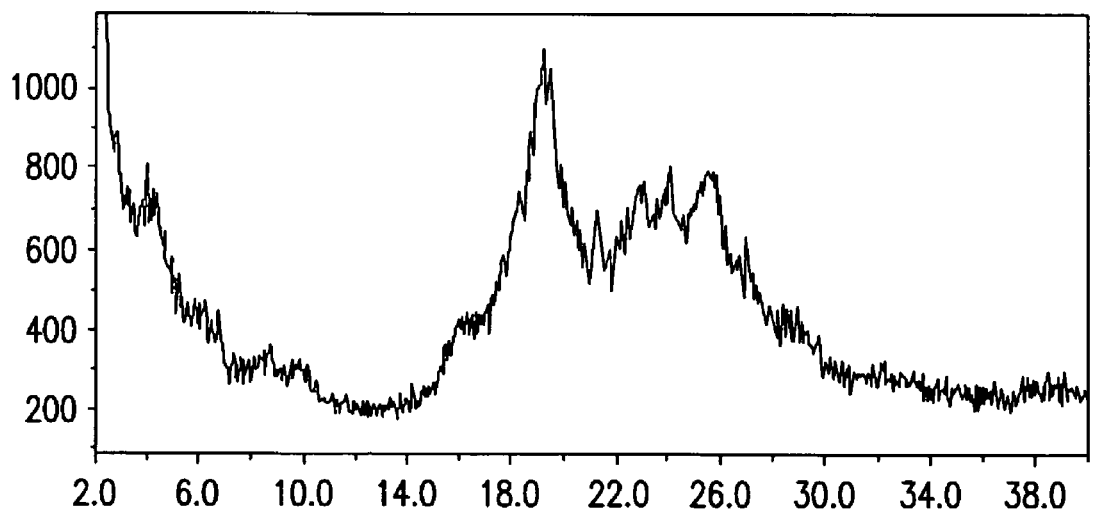
FIG. 20 shows a powder X-ray diffraction pattern for Form XI of lapatinib ditosylate, as obtained in Example 14.

In one embodiment, the present invention encompasses Form XI of lapatinib ditosylate as characterized by a PXRD pattern illustrated in FIGS. 18-20.

In another embodiment, the invention encompasses Form XII of lapatinib ditosylate characterized by a PXRD pattern having peaks at about 5.4, 18.3, 19.1, 24.7, and 25.8±0.3 degrees 2-theta. Preferably, Form XII is substantially amorphous.

Figure 21:
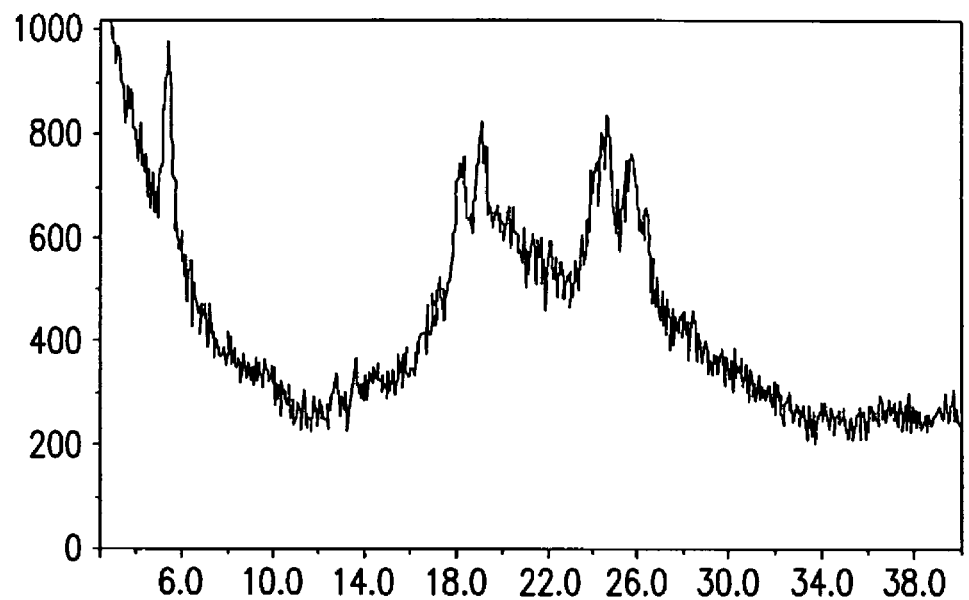
FIG. 21 shows a powder X-ray diffraction pattern for Form XII of lapatinib ditosylate.
Figure 22:
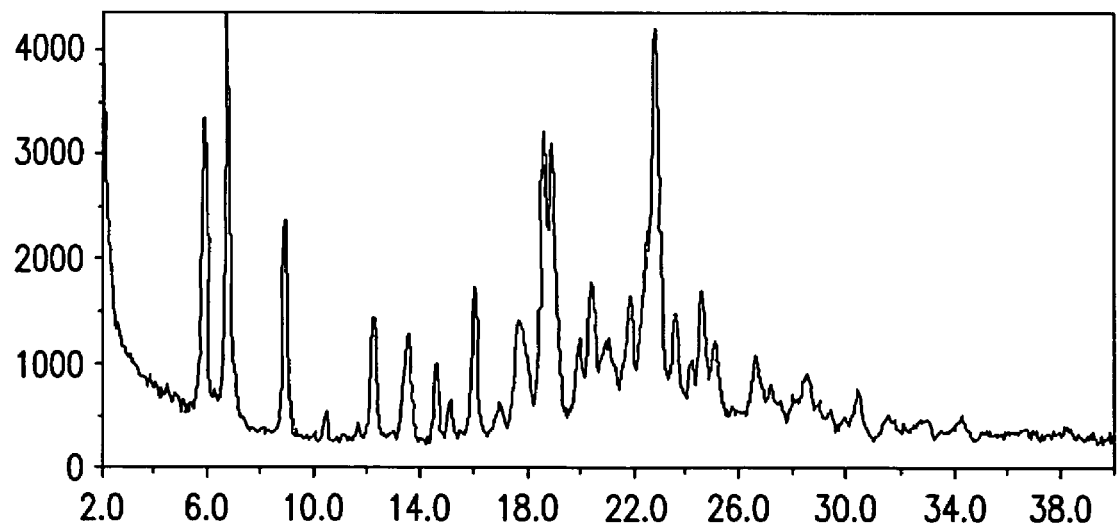
FIG. 22 shows a powder X-ray diffraction pattern for Form XIII of lapatinib ditosylate.

In another embodiment, the present invention encompasses Form XII of lapatinib ditosylate as characterized by a PXRD pattern illustrated in FIG. 21.

In another embodiment, the invention encompasses crystalline Form XIII of lapatinib ditosylate characterized by data selected from the group consisting of a PXRD pattern having peaks at about 5.9, 6.8, and 8.9±0.2 degrees 2-theta, and at least two peaks from the following list: 12.2, 13.5, 16.0, 18.7 and 22.9±0.2 degrees 2-theta; a PXRD pattern having peaks at about 5.9, 6.8, 8.9, 12.2 and 13.6±0.2 degrees 2-theta; a PXRD pattern having peaks at about 5.9, 6.8, 8.9, 12.2, 13.6, 14.6, 16.0, 19.0, 20.4 and 22.9±0.2 degrees 2-theta; a solid-state $^{13}$C NMR spectrum with signals at about 125.1, 129.6 and 150.7±0.2 ppm; a solid-state $^{13}$C NMR spectrum having chemical shifts differences between the signal exhibiting the lowest chemical shift and another in the chemical shift range of 100 to 180 ppm of about 17.2, 21.7 and 42.8±0.1 ppm, wherein the signal exhibiting the lowest chemical shift in the chemical shift area of 100 to 180 ppm is typically at about 107.9+1 ppm.

Figure 23:
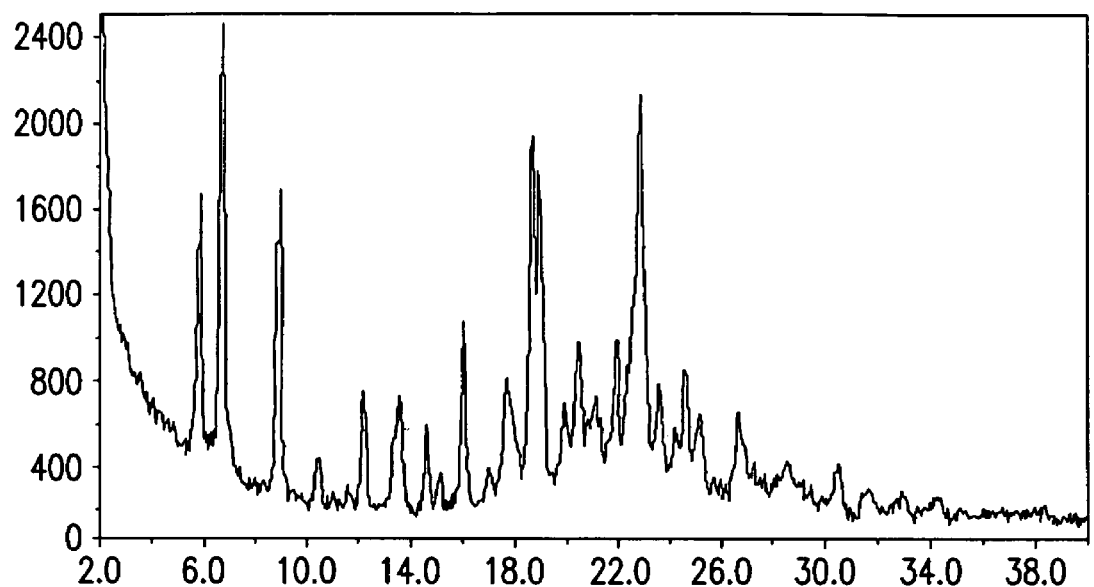
FIG. 23 shows a powder X-ray diffraction pattern for Form XIII of lapatinib ditosylate, as obtained in Example 76.
Figure 24:
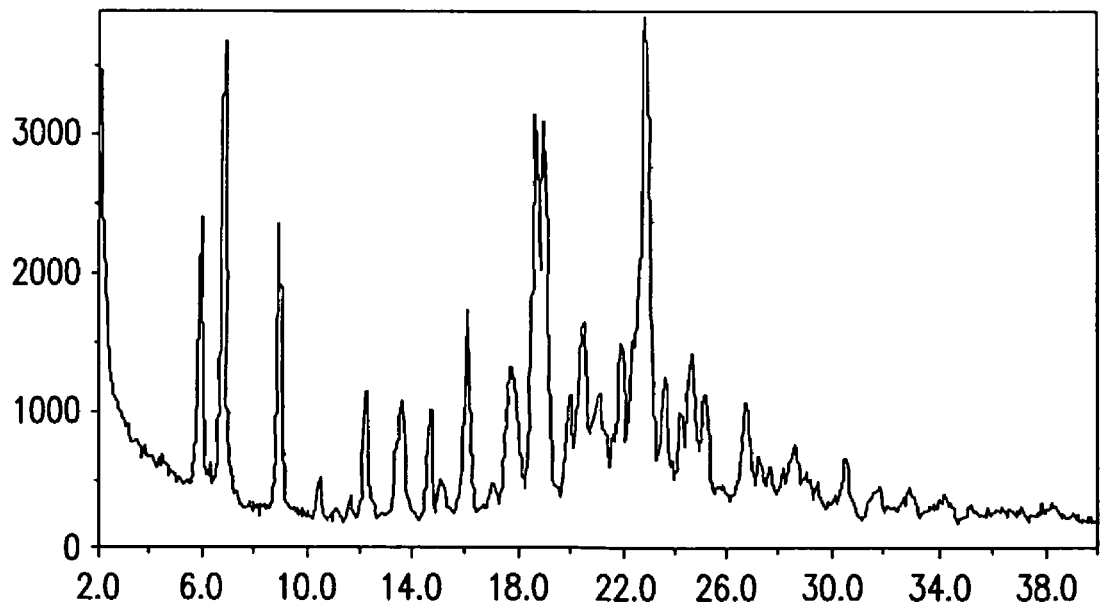
FIG. 24 shows a powder X-ray diffraction pattern for Form XIII of lapatinib ditosylate, as obtained in Example 78.

In another embodiment, the present invention encompasses crystalline Form XIII of lapatinib ditosylate as characterized by a PXRD pattern illustrated in FIG. 23.

Figure 35:
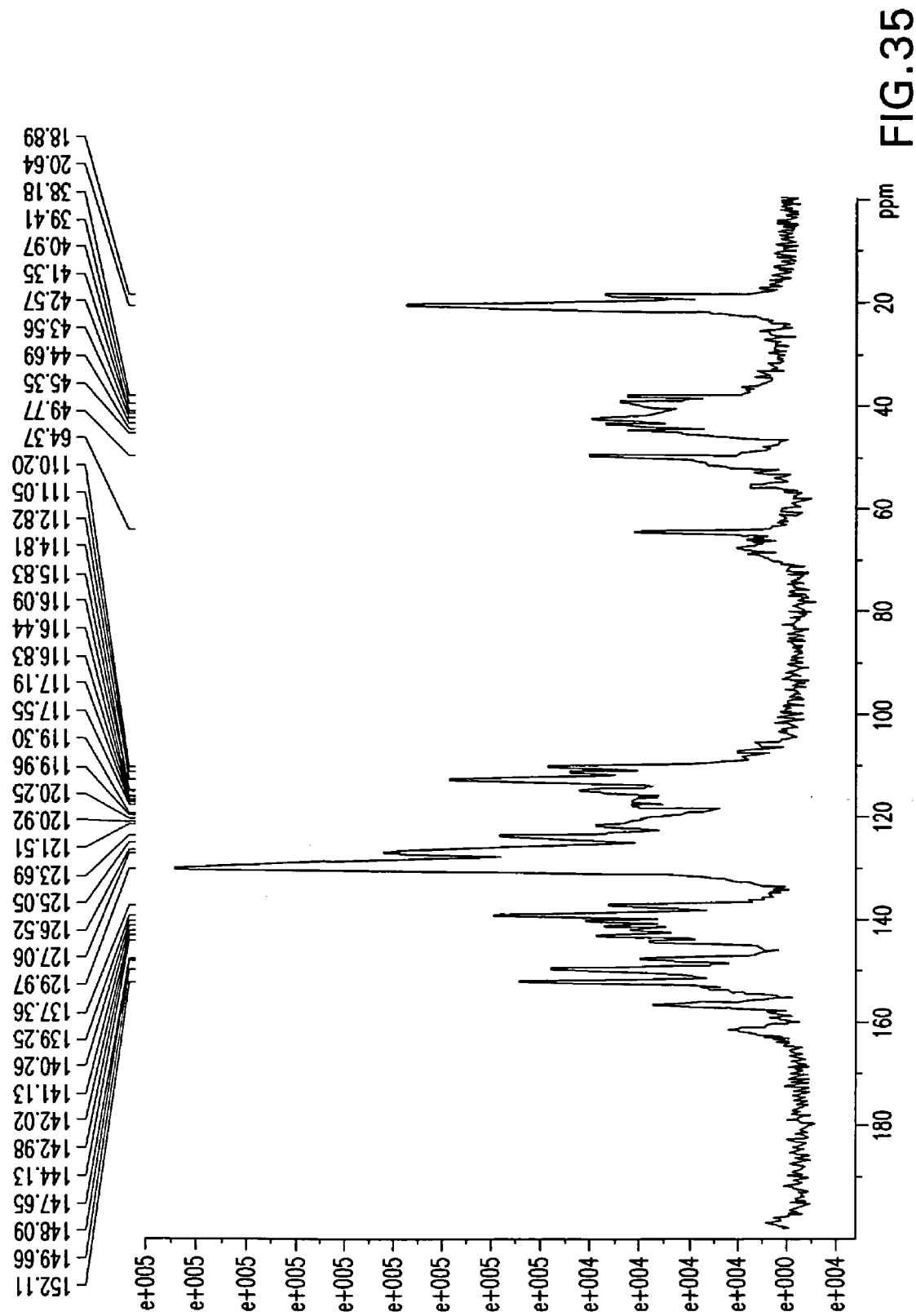
FIG. 35 shows a solid-state $^{13}$C NMR spectrum of lapatinib ditosylate Form I in the 0-200 ppm range.
Figure 36:
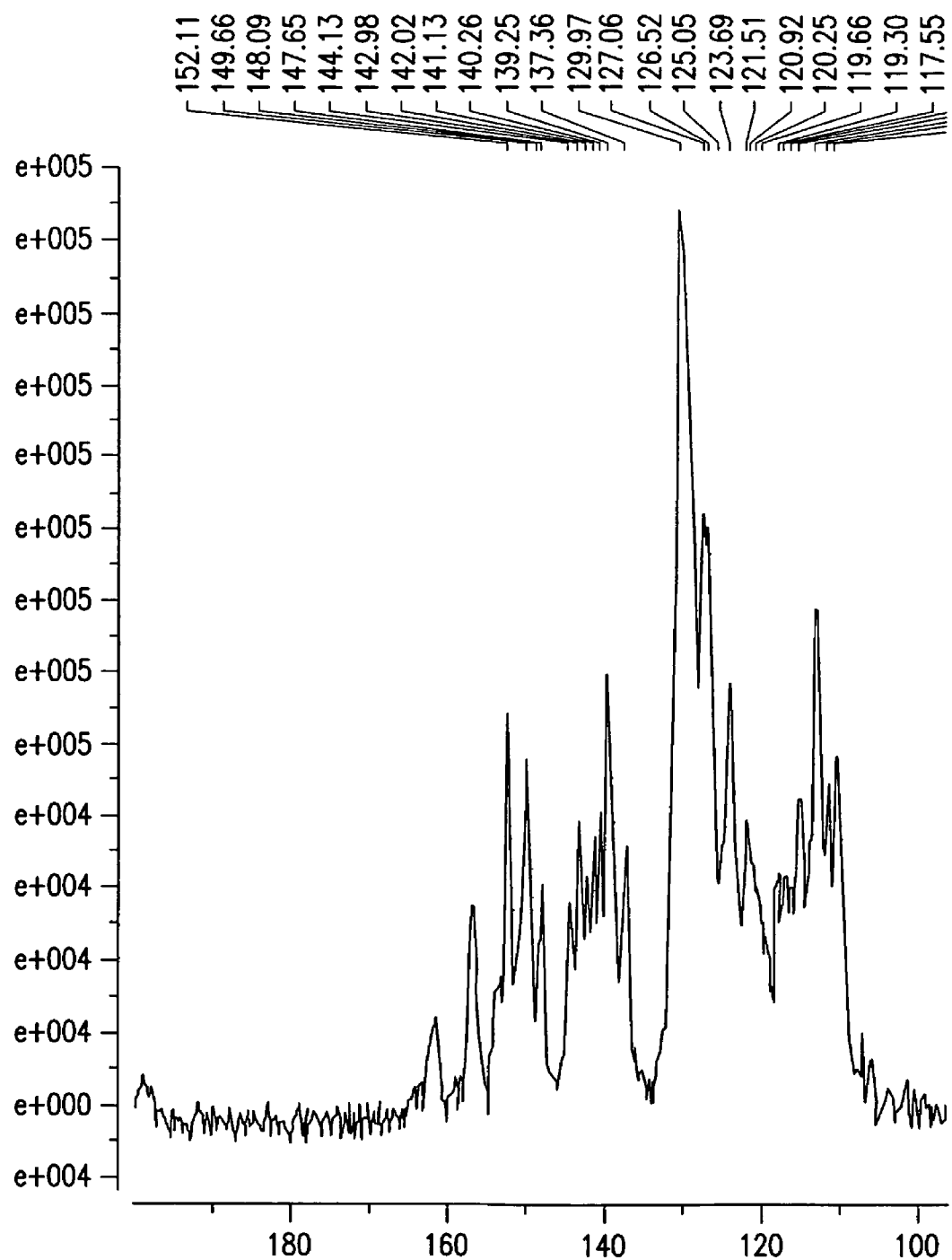
FIG. 36 shows a solid-state $^{13}$C NMR spectrum of lapatinib ditosylate Form I in the 100-200 ppm range.
Figure 37:
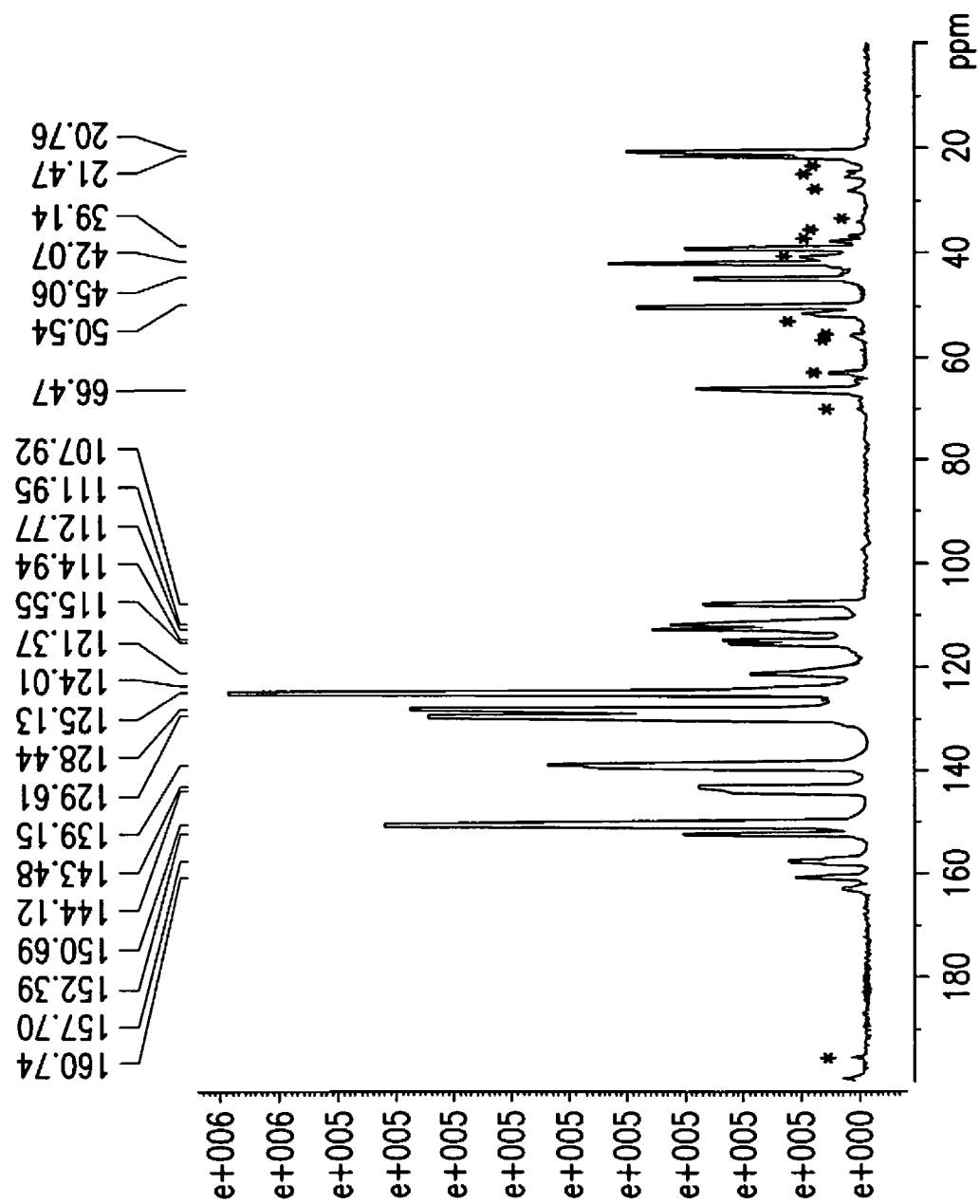
FIG. 37 shows a solid-state $^{13}$C NMR spectrum of lapatinib ditosylate Form XIII in the 0-200 ppm range.
Figure 38:
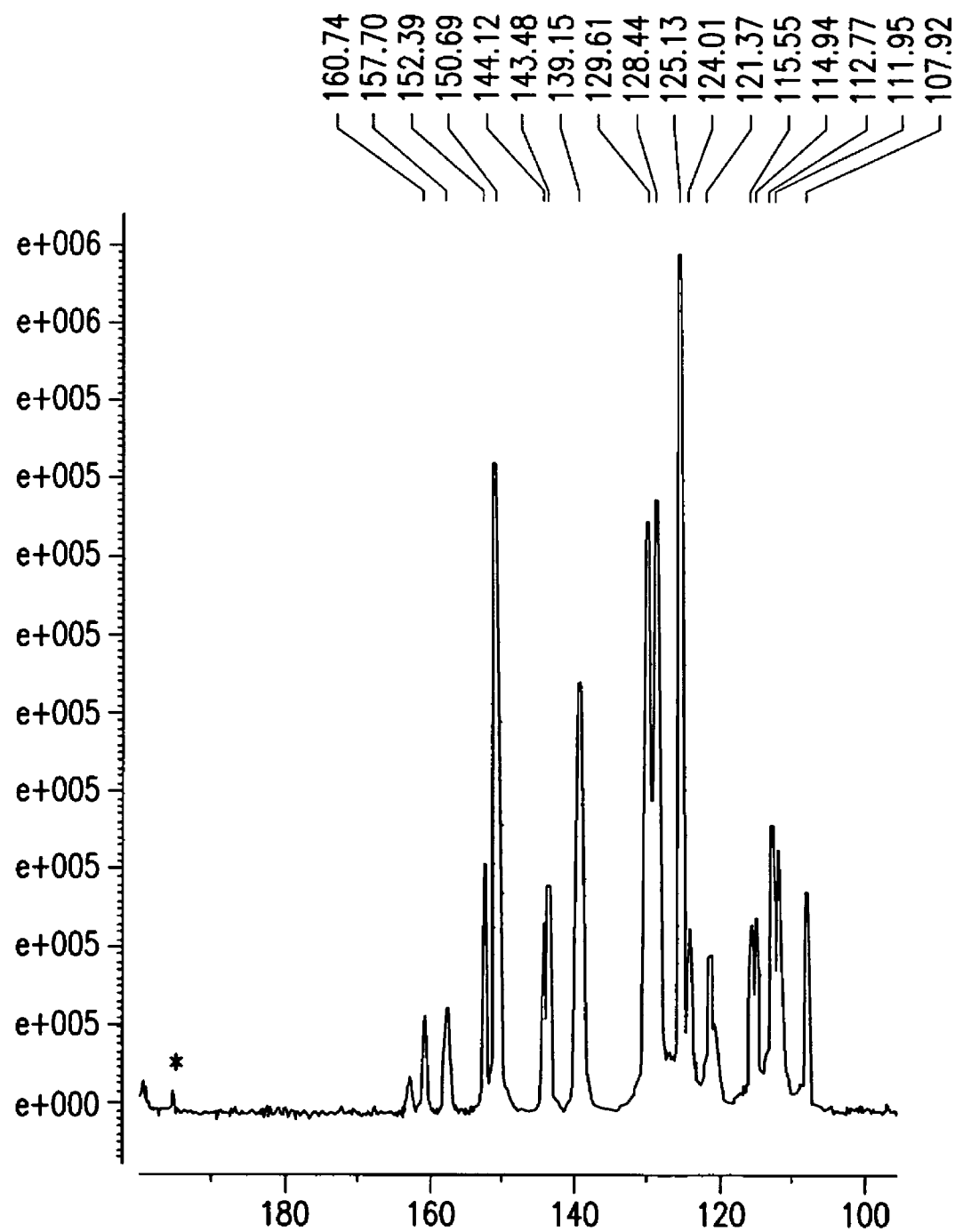
FIG. 38 shows a solid-state $^{13}$C NMR spectrum of lapatinib ditosylate Form XIII in the 100-200 ppm range.

In another embodiment, the present invention encompasses crystalline Form XIII of lapatinib ditosylate as characterized by a solid-state $^{13}$C NMR spectrum illustrated in FIGS. 35, and 36.

In another embodiment, the invention encompasses crystalline Form XIV of lapatinib ditosylate characterized by a PXRD pattern having peaks at about 6.0, 16.9, and 17.5±0.2 degrees 2-theta, and at least two peaks from the following list: 18.7, 19.6, 21.5, 23.3 and 24.0±0.2 degrees 2-theta.

Figure 25:
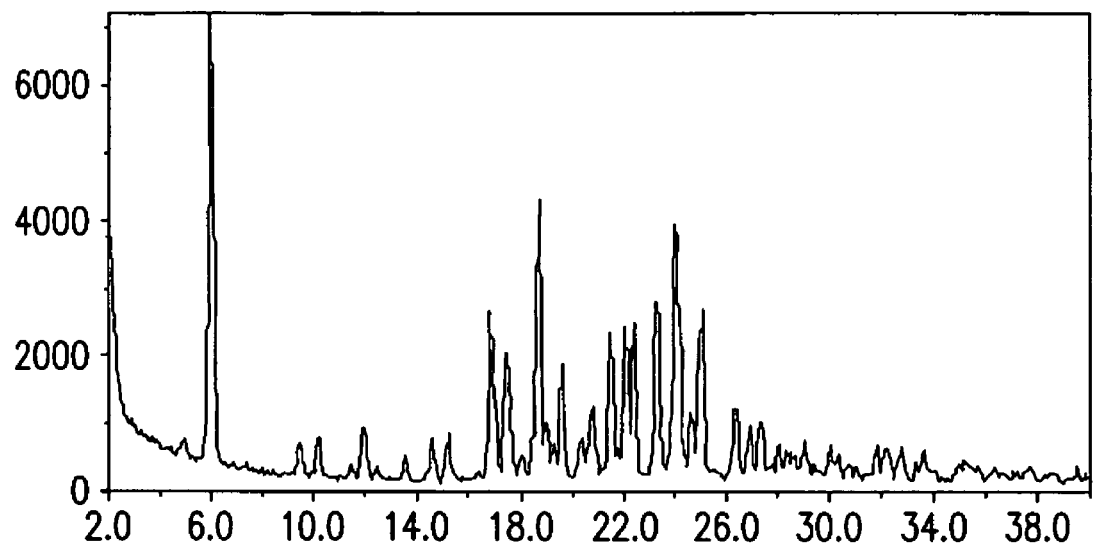
FIG. 25 shows a powder X-ray diffraction pattern for Form XIV of lapatinib ditosylate.

In another embodiment, the present invention encompasses crystalline Form XIV of lapatinib ditosylate as characterized by a PXRD pattern illustrated in FIG. 25.

In another embodiment, the invention encompasses crystalline Form XV of lapatinib ditosylate characterized by data selected from the group consisting of: a PXRD pattern having peaks at about 6.2, 7.0, 8.9, 12.9, and 16.1+0.2 degrees 2-theta; a PXRD pattern having peaks at about 6.2, 7.0, 8.9, 12.9, 16.1, 17.0, 18.9, 19.9, 23.7 and 26.0; a solid-state $^{13}$C NMR spectrum with signals at about 125.1, 128.3 and 137.1+0.2 ppm; and a solid-state $^{13}$C NMR spectrum having chemical shifts differences between the signal exhibiting the lowest chemical shift and another in the chemical shift range of 100 to 180 ppm of about 17.2, 20.3 and 29.2±0.1 ppm, wherein the signal exhibiting the lowest chemical shift in the chemical shift area of 110 to 180 ppm is typically at about 107.9±1 ppm.

Figure 32:
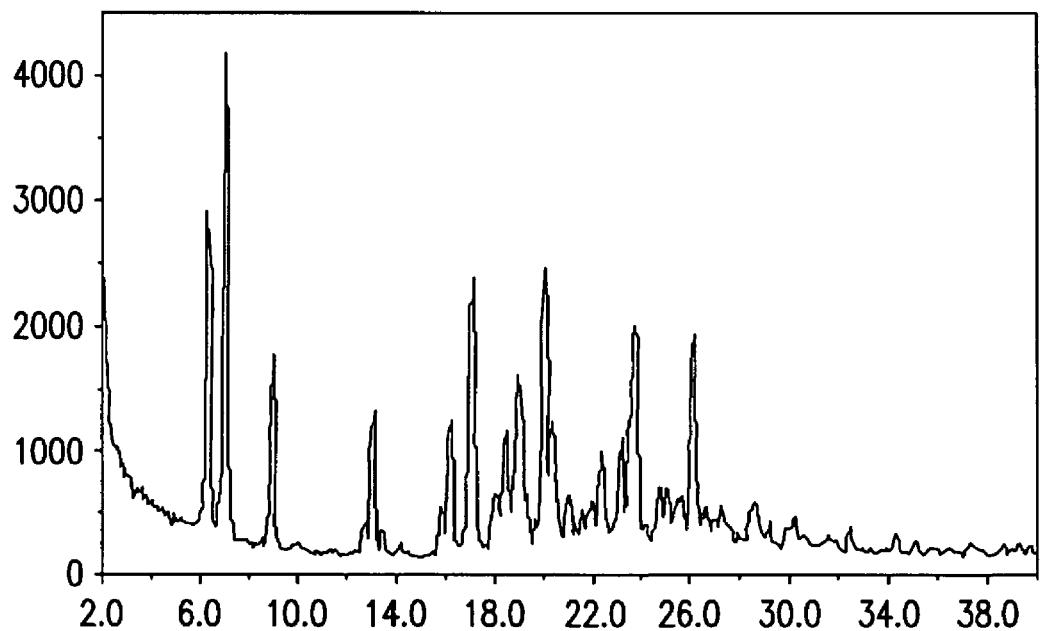
FIG. 32 shows a powder X-ray diffraction pattern for Form XV of lapatinib ditosylate.

In another embodiment, the present invention encompasses crystalline Form XV of lapatinib ditosylate as characterized by a PXRD pattern illustrated in FIG. 32.

Figure 39:
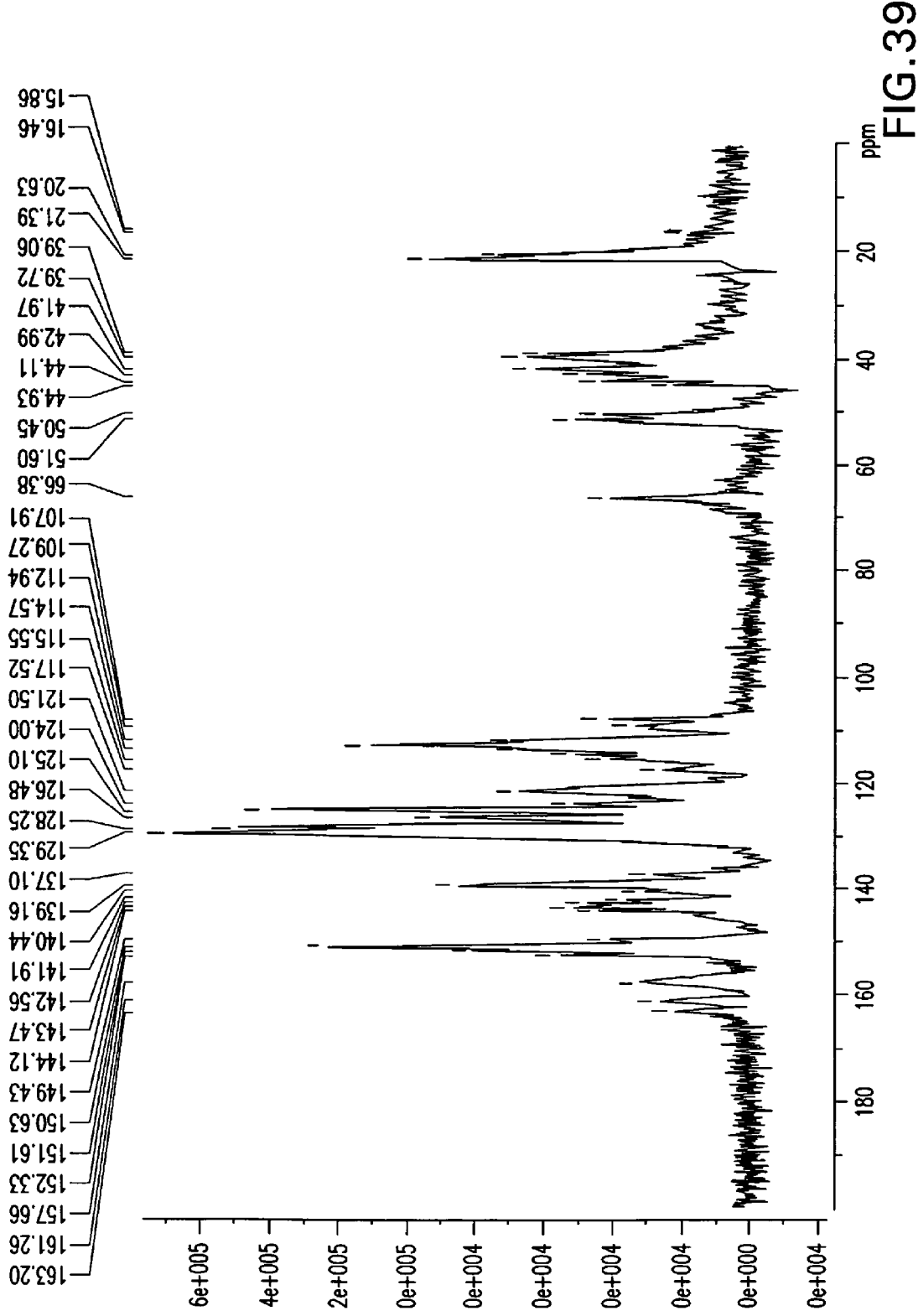
FIG. 39 shows a solid-state $^{13}$C NMR spectrum of lapatinib ditosylate Form XV in the 0-200 ppm range.
Figure 40:
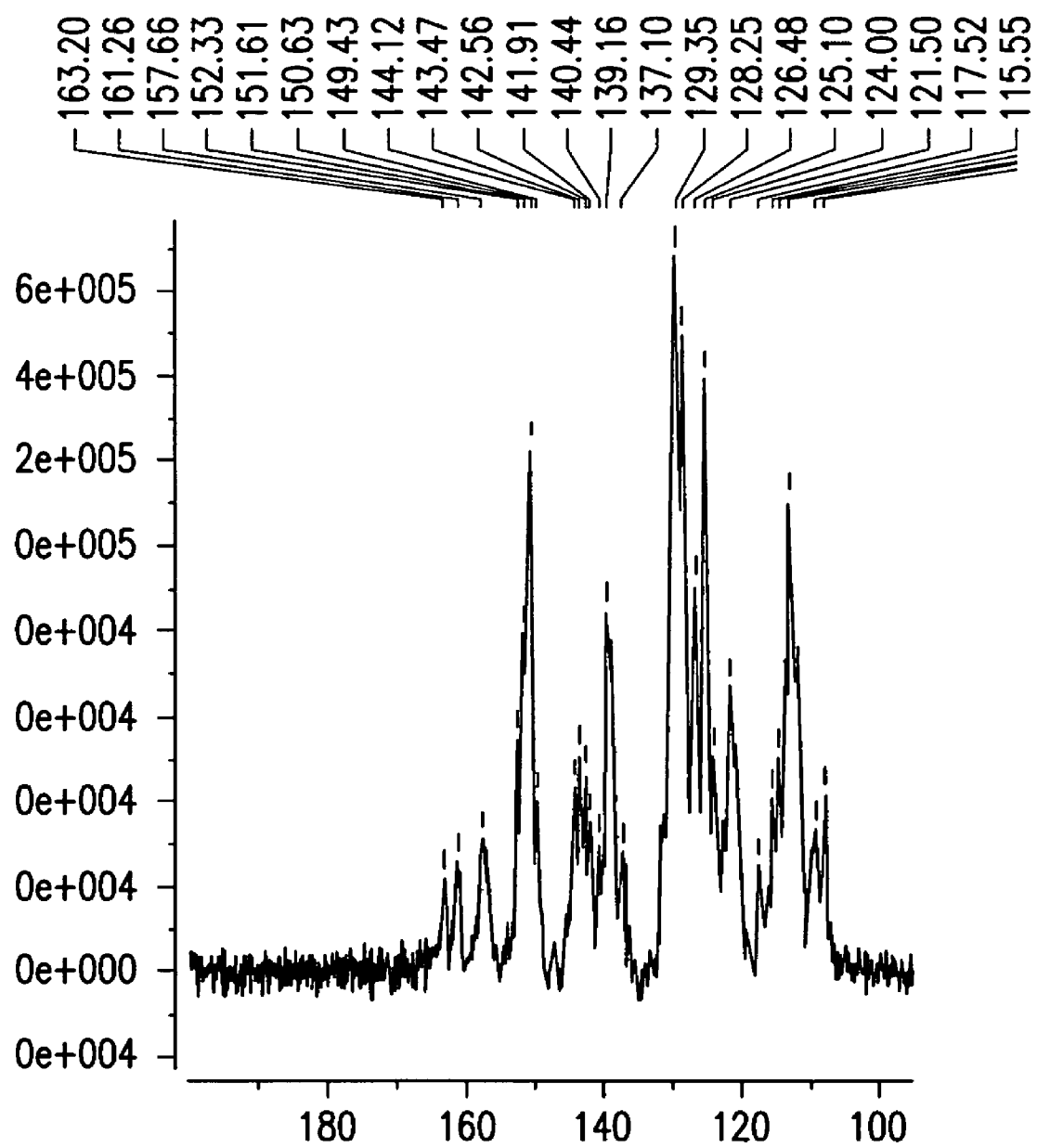
FIG. 40 shows a solid-state $^{13}$C NMR spectrum of lapatinib ditosylate Form XV in the 100-200 ppm range.

In another embodiment, the present invention encompasses crystalline Form XV of lapatinib ditosylate as characterized by a solid-state $^{13}$C NMR spectrum illustrated in FIGS. 39, and 40.

The crystalline form of lapatinib ditosylate, Form XV, is also substantially free of any other polymorphic forms. By "substantially free" is meant 20% (w/w) or less, preferably 10% (w/w) or less, more preferably 5% (w/w) or less, most preferably 2% (w/w) or less, particularly 1% (w/w) or less, more particularly 0.5% (w/w) or less, and most particularly 0.2% (w/w) or less.

In another embodiment, the invention encompasses Form XVI of lapatinib ditosylate characterized by a PXRD pattern having peaks at about 5.3, and 6.3±0.2 degrees 2-theta, and at least three peaks selected from the group consisting of 8.5, 17.0, 18.4, 21.2 and 25.0±0.2 degrees 2-theta.

Figure 27:
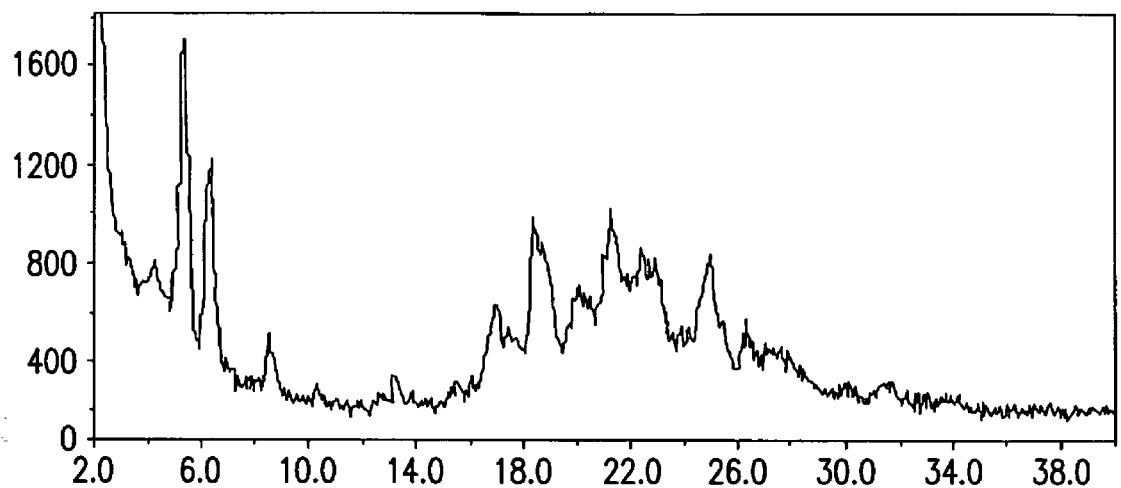
FIG. 27 shows a powder X-ray diffraction pattern for Form XVI of lapatinib ditosylate.

In another embodiment, the present invention encompasses Form XVI of lapatinib ditosylate as characterized by PXRD patterns illustrated in FIG. 27.

In another embodiment, the invention encompasses Form XVII of lapatinib ditosylate characterized by a PXRD pattern having peaks at about 3.3, 4.8, and 7.9±0.2 degrees 2-theta, and a broad peak with maximum at about 22.7 degrees 2-theta.

Figure 28:
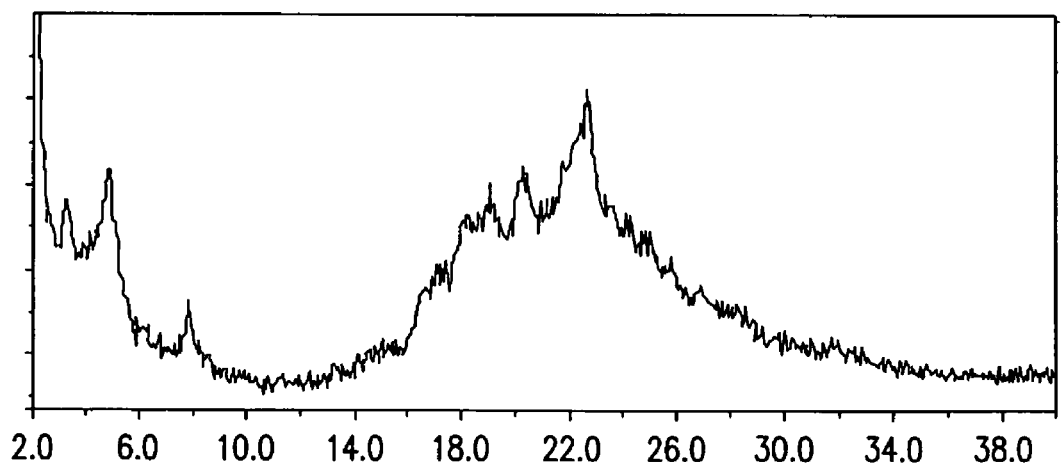
FIG. 28 shows a powder X-ray diffraction pattern for Form XVII of lapatinib ditosylate, as obtained in Example 82.
Figure 29:
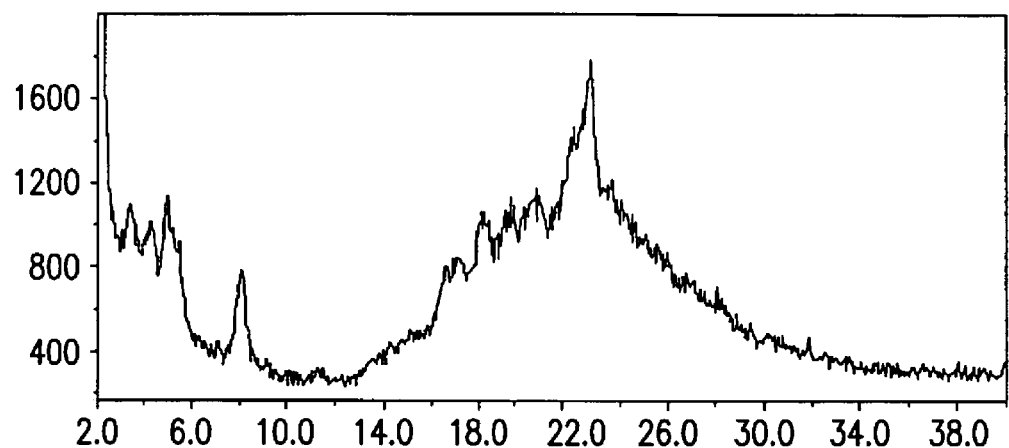
FIG. 29 shows a powder X-ray diffraction pattern for Form XVII of lapatinib ditosylate, as obtained in Example 83.
Figure 30:
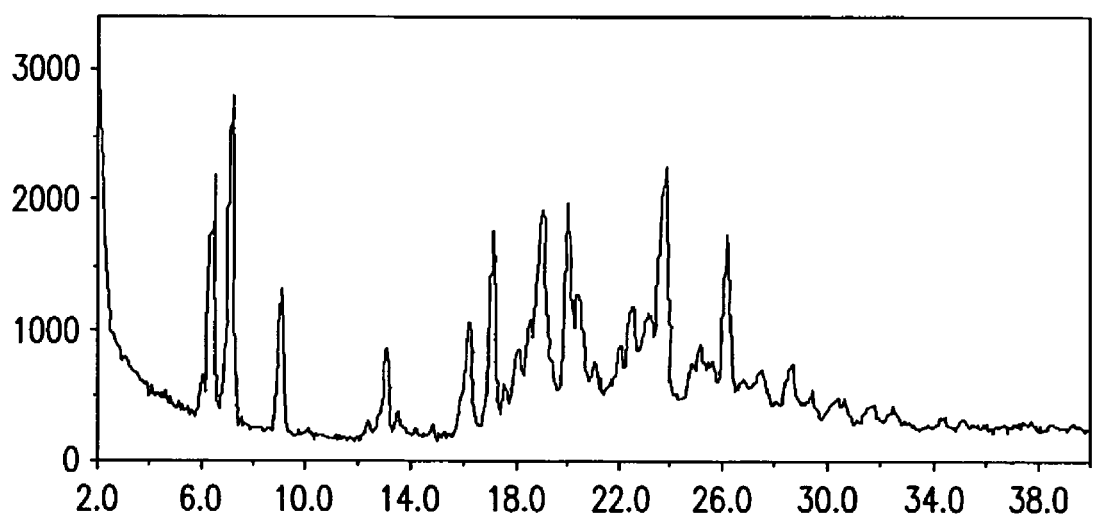
FIG. 30 shows a powder X-ray diffraction pattern for Form XV of lapatinib ditosylate, as obtained in Example 86.
Figure 31:
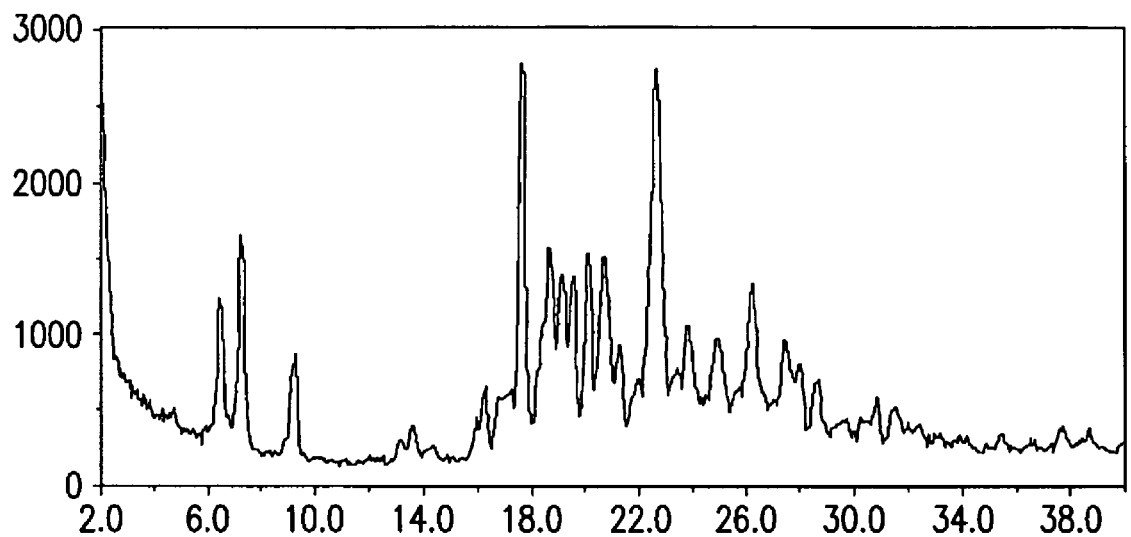
FIG. 31 shows a powder X-ray diffraction pattern for Form XIX of lapatinib ditosylate, as obtained in Example 87.

In another embodiment, the present invention encompasses Form XVII of lapatinib ditosylate as characterized by PXRD patterns illustrated in FIGS. 28 and 29.

In another embodiment, the invention encompasses crystalline Form XVIII of lapatinib ditosylate characterized by a PXRD pattern having peaks at about 5.6, 13.1, 16.0, 16.9 and 23.6±0.2 degrees 2-theta. Form XVIII is further characterized by a PXRD pattern having peaks at about 5.6, 7.4, 13.1, 14.7, 15.2, 16.0, 16.9, 19.8, 20.4 and 23.6±0.2 degrees 2-theta.

In another embodiment, the present invention encompasses crystalline Form XVIII of lapatinib ditosylate as characterized by PXRD patterns illustrated in FIG. 33.

In another embodiment, the invention encompasses crystalline Form XIX of lapatinib ditosylate characterized by data selected from the group consisting of: a PXRD pattern having peaks at about 6.3, 7.1, and 9.0±0.2 degrees 2-theta, and at least two peaks from the following list: 17.5, 19.0, 20.0, 22.5 and 26.0±0.2 degrees 2-theta; a PXRD pattern having peaks at about 6.3, 7.1, 9.0, 17.5, 19.0, and 22.5±0.2 degrees 2-theta; a PXRD pattern having peaks at about 6.3, 7.1, 9.0, 17.5, 18.5, 19.0, 19.4, 20.0, 22.5, and 26.0±0.2 degrees 2-theta.

Figure 26:
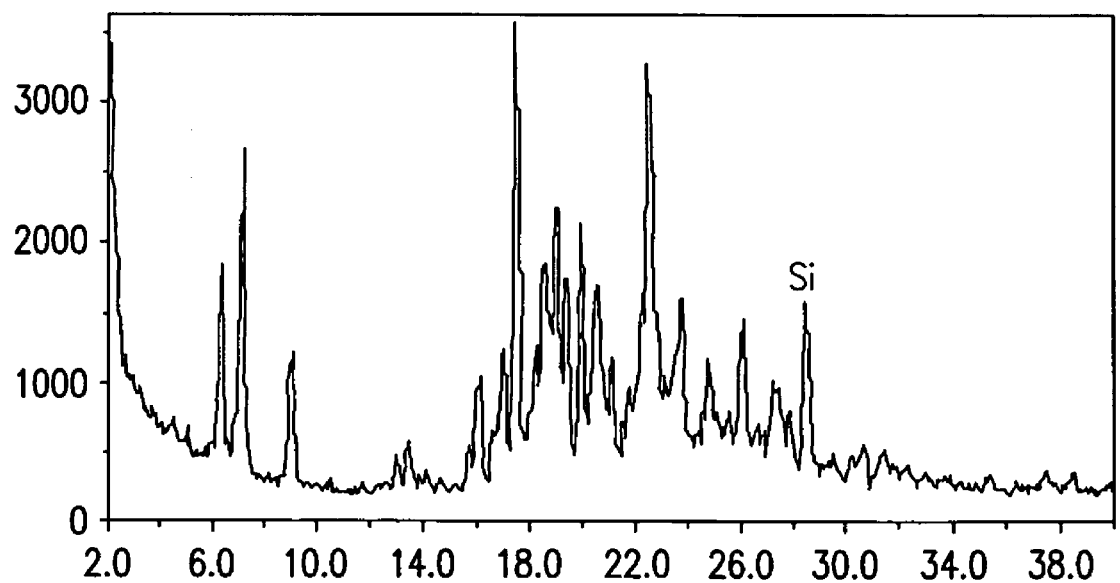
FIG. 26 shows a powder X-ray diffraction pattern for Form XIX of lapatinib ditosylate.

In another embodiment, the present invention encompasses crystalline Form XIX of lapatinib ditosylate as characterized by a PXRD pattern illustrated in FIG. 26.

In one embodiment, the present invention encompasses a process for preparing Form I of lapatinib ditosylate comprising combining lapatinib base, preferably Form X, with p-toluenesulfonic acid (PTSA) under neat conditions to obtain Form I of lapatinib ditosylate.

The mixture is preferably maintained at a temperature of about 0° C. to about 60° C., more preferably about room temperature to about 40° C., most preferably about room temperature, preferably for about 16 hours to about 66 hours, more preferably about 16 hours to about 24 hours, and most preferably about 16 hours. Recovering the product may be carried out by any known method such as filtration.

In another embodiment, the invention encompasses another process for preparing Form I of lapatinib ditosylate comprising combining lapatinib base, p-toluenesulfonic acid, and a solvent selected from the group consisting of heptane and hexane to form a slurry; recovering the obtained precipitate.

The slurry is preferably maintained at about room temperature to about 40° C., most preferably about room temperature, preferably for about 2 hours to about 66 hours, more preferably about 16 hours to about 24 hours, and most preferably about 16 hours. Recovering the product may be carried out by any known method such as filtration.

The obtained precipitate may be further heated to about 40° C. to about 70° C., under reduced pressure.

In another embodiment, the invention encompasses a process for preparing Form iI of lapatinib ditosylate comprising forming a solution of lapatinib ditosylate with an organic solvent selected from the group consisting of dimethylacetamide (DMA), and dimethylformamide (DMF); adding an antisolvent selected from the group consisting of toluene, methyl-tert butyl ether (MTBE), and heptane; and recovering of the crystalline form.

In one specific embodiment, the pair of solvents and antisolvents can be selected from the group consisting of: DMA/toluene, DMA/MTBE, DMA/heptane, and DMF/toluene.

The mixture is preferably maintained at a temperature of about 0° C. to about 60° C., more preferably about 20° C. to about 40° C., even more preferably, about 20° C. to about 30° C., most preferably about 25° C., preferably, for about 1 hour to about 18 hours, more preferably about 1 hour to about 6 hours. Recovering the product may be carried out by any known method such as filtration.

Preferably, lapatinib ditosylate is prepared in situ comprising combining lapatinib base and p-toluenesulfonic acid.

In another embodiment, the present invention encompasses another process for preparing Form iI of lapatinib ditosylate comprising combining lapatinib ditosylate with dimethylformamide to form a slurry; and recovering the crystalline form.

Typically, the mixture is maintained at a temperature of about room temperature, preferably for about 30 minutes to about 24 hours, more preferably for about 30 minutes to about 12 hours, even more preferably for about 30 minutes to about 6 hours, and most preferably for about 2 hours.

In another embodiment, the invention encompasses a process for preparing Form III of lapatinib ditosylate comprising forming a solution of lapatinib ditosylate and dimethylformamide; adding an antisolvent selected from the group consisting of acetone, and tetrahydrofuran (THF); and recovering the precipitate.

The mixture is preferably maintained at a temperature of about 0° C. to about 65° C., more preferably about 20° C. to about 40° C., even more preferably about 20° C. to about 30° C., preferably, for about 1 hour to about 18 hours, and more preferably for about 1 hour to about 6 hours. Recovering the product may be carried out by any known method such as filtration.

Preferably, lapatinib ditosylate is prepared in situ comprising combining lapatinib base and p-toluenesulfonic acid.

In another embodiment, the invention encompasses a process for preparing Form IV of lapatinib ditosylate comprising forming a solution of lapatinib ditosylate and dimethylformamide; adding acetonitrile; and recovering the product.

The mixture is preferably maintained at a temperature of about 0° C. to about 90° C., more preferably about 20° C. to about 50° C., even more preferably about 20° C. to about 30° C., preferably, for about 1 hour to about 18 hours, more preferably for about 1 hour to about 6 hours. Recovering the product may be carried out by any known method such as filtration.

Preferably, lapatinib ditosylate is prepared in situ comprising combining lapatinib base and p-toluenesulfonic acid.

In another embodiment, the invention encompasses a process for preparing Form V of lapatinib ditosylate comprising forming a solution of lapatinib ditosylate and an organic solvent selected from the group consisting of N-methylpyrrolidone (NMP), and DMF; adding an antisolvent selected from the group consisting of hexane, acetone, tetrahydrofuran, acetonitrile, isopropanol (IPA), and methyl-tert butyl ether; and recovering the product. The pair of solvents and antisolvents can be selected from the group consisting of: N-methylpyrrolidone/hexane, N-methylpyrrolidone/isopropanol, N-methylpyrrolidone/acetone, N-methylpyrrolidone/tetrahydrofuran, N-methylpyrrolidone/MTBE, and N-methylpyrrolidone/acetonitrile.

Preferably, lapatinib ditosylate is prepared in situ comprising combining lapatinib base and p-toluenesulfonic acid.

The mixture is preferably maintained at a temperature of about 0° C. to about 60° C., more preferably about 20° C. to about 40° C., even more preferably about 20° C. to about 30° C. for about 1 hour to about 18 hours. Recovering the product may be carried out by any known method such as filtration.

In another embodiment, the present invention encompasses another process for preparing Form V of lapatinib ditosylate comprising combining lapatinib ditosylate with N-methylpyrrolidone to form a slurry; and recovering the precipitate.

Typically, the mixture is maintained at a temperature of about 0° C. to about 90° C., more preferably about 20° C. to about 50° C., even more preferably about 20° C., to about 30° C., preferably for about an hour to about 6 hours, more preferably for about 30 minutes to about 24 hours, more preferably for about 30 minutes to about 12 hours, even more preferably for about 30 minutes to about 6 hours, and most preferably for about 2 hours.

In another embodiment, the present invention encompasses a process for preparing Form VI of lapatinib ditosylate comprising forming a solution of lapatinib ditosylate in dimethylformamide; and precipitating Form VI. Precipitation can be carried out comprising: cooling the solution, or concentrating the solution, or by seeding with lapatinib ditosylate Form VI, or by adding an antisolvent selected from the group consisting of MTBE, hexane, and heptane.

In one specific example, lapatinib ditosylate is prepared in situ comprising dissolving lapatinib base and p-toluenesulfonic acid in dimethylformamide.

Preferably, the solution of lapatinib base in dimethylformamide is heated to about 40° C. to about 60° C., more preferably to about 40° C., prior to the addition of the acid. When cooling is applied in order to induce precipitation, preferably, the obtained mixture is cooled to about −10° C. to about 25° C., more preferably to about −10° C. to about 15° C., and most preferably to about 0° C. to about 10° C.

The obtained Form VI can be further recrystallized comprising forming a slurry of the obtained Form VI of lapatinib ditosylate in dimethylformamide. Slurrying the obtained Form VI results with higher chemichal purity of the lapatinib ditosylate Form VI. Preferably, the chemichal purity of the lapatinib ditosylate Form VI before slurrying in dimethylformamide is at least 98%. Preferably, the chemichal purity of the lapatinib ditosylate Form VI after slurrying in dimethylformamide is at least 99%.

Form VI can be further dried to obtain Form XV of lapatinib ditosylate. Preferably, Form VI is dried at a temperature of about 40° C. to about 90° C., more preferably, at about 60° C. to about 70° C., and most preferably about 60° C., preferably under reduced pressure. Preferably the drying is carried out, more preferably, for about 12 hours to about 20 hours, and, most preferably, for 12 hours.

The mixture is preferably maintained at a temperature of about 0° C. to about 60° C., more preferably about 20° C. to about 40° C., even more preferably about 20° C. to about 30° C. for about 2 hours to about 16 hours, preferably about 2 hours to about 7 hours. Recovering the product may be carried out by any known method such as filtration.

In another embodiment, the present invention encompasses a process for preparing Form VII of lapatinib ditosylate comprising drying Form XI of lapatinib ditosylate, preferably under reduced pressure, or drying Form I of lapatinib ditosylate, preferably, under reduced pressure.

Preferably, drying is carried out at a temperature of about 40° C. to about 80° C., more preferably 40° C. to about 70° C., and most preferably about 40° C. to about 60° C., preferably, for about 8 hours to about 36 hours, more preferably for about 10 hours to about 20 hours, and most preferably for about 12 hours.

In another embodiment, the present invention encompasses a process for preparing Form VII of lapatinib ditosylate comprising combining lapatinib base, preferably Form X, with p-Toluenesulfonic acid in the presence of organic solvent selected from the group consisting of heptane, and methyl tert butyl ether to form a slurry; and drying the obtained precipitate to obtain Form VII of lapatinib ditosylate.

The mixture is preferably maintained at a temperature of about 0° C. to about 60° C., more preferably about 20° C. to about 40° C., even more preferably about 20° C. to about 30° C., preferably, for about 30 minutes to about 24 hours, more preferably for about 30 minutes to about 12 hours, even more preferably for about 30 minutes to about 6 hours, and most preferably for about 2 hours. Recovering the product may be carried out by any known method such as filtration.

Preferably, the obtained Form VII is dried at a temperature of about 40° C. to about 60° C., more preferably for about 40° C. to about 50° C., preferably for about 8 hours to about 36 hours, more preferably, for about 10 hours to about 20 hours, and most preferably for about 12 hours.

In another embodiment, the present invention encompasses a process for preparing Form VIII of lapatinib ditosylate comprising forming a solution of lapatinib base in DMA; adding p-toluenesulfonic acid; and recovering the obtained precipitate.

Preferably, lapatinib ditosylate is prepared in situ comprising combining lapatinib base and p-toluenesulfonic acid.

Preferably, the solution of lapatinib base in DMA is heated to about 40° C. to about 60° C., more preferably to about 40° C., prior to the addition of the acid. Preferably, after the addition of the acid, the obtained mixture is cooled to about −10° C. to about 25° C., more preferably to about −10° C. to about 15° C., and most preferably to about 0° C. to about 10° C.

Form VIII can be further dried to obtain Form XIII of lapatinib ditosylate. Preferably, Form VIII is dried at a temperature of about 60° C. to about 90° C., more preferably about 70° C. to about 90° C., preferably under reduced pressure. Preferably the drying is carried out overnight, more preferably, for about 12 hours to about 20 hours, and, most preferably, for 12 hours.

In another embodiment, the invention encompasses a process for preparing Form VIII of lapatinib ditosylate comprising forming a solution of lapatinib ditosylate and dimethylacetamide; adding hexane; and recovering the product.

The mixture is preferably maintained at a temperature of about 0° C. to about 70° C., more preferably about 20° C. to about 50° C., and most preferably about 20° C. to about 30° C., preferably, for about 1 hour to about 18 hours, more preferably, for about an hour to about 6 hours. Recovering the product may be carried out by any known method such as filtration.

Preferably, lapatinib ditosylate is prepared in situ comprising combining lapatinib base and p-toluenesulfonic acid.

In another embodiment, the present invention encompasses a process for preparing Form IX of lapatinib ditosylate comprising combining lapatinib base, preferably, lapatinib base Form X, with p-toluenesulfonic acid in the presence of diethyl ether; and drying the obtained precipitate to obtain Form IX of lapatinib ditosylate.

The mixture is preferably maintained at a temperature of about 0° C. to about 35° C., more preferably about 20° C. to about 30° C., and most preferably about 25° C., preferably, for about 1 hour to about 18 hours. Recovering the product may be carried out by any known method such as filtration.

Preferably, the obtained Form IX is dried at a temperature of about 30° C. to about 60° C., more preferably 40° C. to about 60° C., and most preferably about 40° C. to about 50° C., preferably for about 8 hours to about 36 hours, more preferably, for about 10 hours to about 20 hours, and most preferably for about 12 hours.

In another embodiment, the present invention encompasses a process for preparing Form XI of lapatinib ditosylate comprising melting lapatinib ditosylate by heating; and cooling the lapatinib ditosylate to obtain Form XI.

Preferably, the lapatinib is heated to about 100° C. to about 120° C. for about 0.5 hour. Preferably, the lapatinib ditosylate is cooled to about room temperature.

In another embodiment, the present invention encompasses a process for preparing Form XI of lapatinib ditosylate comprising grinding lapatinib ditosylate, preferably lapatinib ditosylate Form I, in the presence of a solvent (about one drop) selected from the group consisting of ethanol, and isopropanol.

The term "grinding" broadly refers to crushing a compound, typically using a mortar and pestle.

In another embodiment, the present invention encompasses a process for preparing Form XI of lapatinib ditosylate comprising dissolving lapatinib ditosylate in dimethyl sulfoxide; and removing the solvent by lyophilization.

Preferably, lapatinib ditosylate is prepared in situ comprising combining lapatinib base and p-toluenesulfonic acid.

Typically, lyophilization is done by a process comprising cooling the solution to obtain a cooled mixture, and evaporating the solvent while maintaining the mixture cooled at low temperature.

Preferably, the solution is cooled to a temperature of about −30° C. to about −40° C., providing the cooled mixture, which is a frozen mass.

Typically, the frozen mass is then subjected to a pressure of less than about one atmosphere, to remove the solvent.

In another embodiment, the present invention encompasses another process for Form XI of lapatinib ditosylate comprising forming a slurry of lapatinib base, PTSA, and methyl tert butyl ether; and recovering Form XI of lapatinib ditosylate.

Typically, the mixture is maintained at about 0° C. to about 60° C., more preferably about 20° C. to about 40° C., and most preferably about 20° C. to about 30° C., preferably, for about 30 minutes to about 24 hours, more preferably for about 30 minutes to about 12 hours, even more preferably for about 30 minutes to about 6 hours, and most preferably for about 2 hours.

In another embodiment, the present invention encompasses a process for preparing Form XII of lapatinib ditosylate comprising grinding Form I of lapatinib ditosylate in the presence of water (about one drop).

The precipitate is preferably dried at the elevated temperature for about 16 hours.

In another embodiment, the invention encompasses a process for preparing Form XIII of lapatinib ditosylate comprising forming a solution of lapatinib ditosylate, and dimethylacetamide; adding hexane; and drying the obtained precipitate to obtain Form XIII.

Optionally, lapatinib ditosylate can be prepared in situ comprising combining lapatinib base, and p-toluenesulfonic acid in DMA.

The mixture is preferably maintained at a temperature of about 0° C. to about 70° C., more preferably about 20° C. to about 40° C., and most preferably about 20° C. to about 30° C. for about 2 hours to about 72 hours, more preferably about 2 hours to about 48 hours, and most preferably about 2 hour to about 5 hours. The precipitate is dried at a temperature of about 40° C. to about 90° C., more preferably about 50° C. to about 80° C., even more preferably about 50° C. to about 70° C., and most preferably about 60° C., preferably, for about 10 hours to about 96 hours, more preferably about 10 hours to about 72 hours, and most preferably about 10 hours to about 24 hours to obtain Form XIII.

In another embodiment, the invention encompasses a process for preparing Form XIII of lapatinib ditosylate comprising drying lapatinib ditosylate Form VIII, or lapatinib ditosylate Form VI.

Preferably, Form VIII, or Form VI are dried at a temperature of about 40° C. to about 90° C., more preferably about 40° C. to about 60° C., for about 10 hours to about 96 hours, more preferably about 10 hours to about 72 hours, and most preferably about 30 hours to about 40 hours.

In another embodiment, the invention encompasses a process for preparing Form XIV comprising dissolving lapatinib ditosylate in DMA; adding methanol; and drying the obtained precipitate.

Optionally, lapatinib ditosylate can be prepared in situ comprising combining lapatinib base, preferably Form X, and p-toluenesulfonic acid.

The mixture is preferably maintained at a temperature of about 0° C. to about 70° C., more preferably about 20° C. to about 50° C., and most preferably about 20° C. to about 30° C. for about 1 hour to about 18 hours. Recovering the product may be carried out by any known method such as filtration.

In another embodiment, the invention encompasses a process for preparing lapatinib ditosylate Form XV comprising forming a solution of lapatinib ditosylate in dimethylformamide; adding heptane; and drying the obtained precipitate to obtain Form XV. In one embodiment, the addition of heptane results in a suspension of crystalline lapatinib ditosylate Form VI, and drying the crystalline lapatinib ditosylate Form VI results in crystalline lapatinib ditosylate Form XV. The present invention therefore also encompasses a process for preparing Form XV of lapatinib ditosylate comprising drying Form VI of lapatinib ditosylate. Preferably, after addition of heptane, the obtained suspension is stirred for a suitable period of time to facilate production of lapatinib ditosylate Form XV. The stirring time suitable for production of lapatinib ditosylate Form XV can be determined by a person skilled in the art using routine experimentation. In a preferred embodiment, the suspension is stirred for a period from about 4 hours to about 12 hours, more preferably from about 4 hours to about 8 hours, and most preferably about 5 hours. Preferably, the suspension is stirred at room temperature. Preferably, the drying is carried out at a temperature of about 40° C. to about 90° C., more preferably about 50° C. to about 80° C., even more preferably about 50° C. to about 70° C., and most preferably at about 50° C. under reduced pressure (less than 1 atmosphere).

Optionally, lapatinib ditosylate can be prepared in situ by combining lapatinib base and p-toluenesulfonic acid in dimethylformamide.

The obtained mixture is preferably maintained at about room temperature, preferably for about 2 hours to about 8 hours, more preferably for about 5 hours to about 6 hours.

In another embodiment, the present invention encompasses a process for preparing Form XVI of lapatinib ditosylate comprising forming a suspension of lapatinib base Form X and p-toluenesulfonic acid with methyl isobutyl ketone; and recovering the crystalline form.

The suspension may be stirred at about room temperature for about 20 hours.

In another embodiment, the present invention encompasses a process for preparing Form XVII of lapatinib ditosylate comprising drying lapatinib ditosylate Form XVI.

Preferably, the drying is carried out at elevated temperature, preferably under reduced pressure (less than about 1 atmosphere). Typically, Form XVI is dried at a temperature of about 40° C. for about 120 hours.

In another embodiment, the present invention encompasses a process for preparing Form XVIII of lapatinib ditosylate comprising slurrying lapatinib ditosylate in dimethylformamide; adding tetrahydrofuran; and adding heptane to obtain Form XVIII.

Preferably, the obtained slurry is maintained at about 0° C. to about 70° C., more preferably about 20° C. to about 50° C., and most preferably about 20° C. to about 30° C., preferably for about 10 hours to about 20 hours, more preferably for about 14 hours to about 20 hours, and most preferably for about 16 hours.

In another embodiment, the present invention encompasses a process for preparing Form XIX of lapatinib ditosylate comprising drying Form VI of lapatinib ditosylate at a temperature of about 40° C. to about 90° C., more preferably about 50° C. to about 80° C., even more preferably about 50° C. to about 70° C., and most preferably at about 60° C. under reduced pressure (less than 1 atmosphere). Preferably, the process further comprises forming a solution of lapatinib ditosylate in dimethylformamide; adding heptane to produce a suspension of Form VI of lapatinib ditosylate. Preferably, the obtained suspension is stirred for a suitable period of time to facilate production of lapatinib ditosylate Form XIX. The stirring time suitable for production of lapatinib ditosylate Form XIX can be determined by a person skilled in the art using routine experimentation. In a preferred embodiment, the suspension is stirred for a period from about 18 hours to about 30 hours, more preferably from about 18 hours to about 24 hours, and most preferably about 24 hours. Preferably, the suspension is stirred at 25° C.

The mixture is preferably maintained at a temperature of about 0° C. to about 80° C., more preferably about 20° C. to about 50° C., and most preferably about 20° C. to about 30° C. for about 1 hour to about 18 hours. Recovering the product may be carried out by any known method such as filtration.

In another embodiment, the present invention encompasses a new process for preparing lapatinib ditosylate monohydrate comprising slurrying Lapatinb ditosylate in methanol, water, or a mixture of water and an organic solvent selected from the group consisting of acetone, acetonitrile, methanol, ethanol, and isopropanol; and drying the obtained precipitate. Preferably, the water/solvent ratio is about 40:60 to about 60:40, more preferably about 50:50.

Typically, the mixture is maintained at a temperature of about 0° C. to about 70° C., more preferably about 20° C. to about 50° C., and most preferably about 20° C. to about 25° C., preferably, for about 2 hours to about 18 hours. Preferably, the obtained precipitate is dried at a temperature of about 40° C. to about 70° C., more preferably about 40° C. to about 60° C., and most preferably about 40° C. Preferably, drying is carried out overnight, and most preferably, for about 16 hours.

In another embodiment, the present invention encompasses another process for preparing lapatinib ditosylate monohydrate comprising dissolving lapatinib ditosylate in an organic solvent selected from the group consisting of dimethylacetamide, dimethylformamide, and dimethylsulfoxide; and adding an anti solvent selected from the group consisting of hexane, tetrahydrofuran, ethyl acetate, acetonitrile, isopropanol, and acetone, wherein, if dimethylformamide or dimethylsulfoxide are used as the organic solvent, the precipitate is dried at elevated temperature under reduced pressure. The pair of solvents and antisolvents can be selected from the group consisting of: DMA/tetrahydrofuran, DMA/ethyl acetate, DMA/acetone, DMA/acetonitrile, DMA/isopropanol.

Preferably the reaction mixture is maintained at about 0° C. to about 70° C., more preferably about 20° C. to about 40° C., and most preferably at about room temperature, preferably, for about an hour to about 16 hours. The precipitate is preferably dried at an elevated temperature, preferably under reduced pressure. For example, drying can be carried out at a temperature of about 40° C. to about 90° C., more preferably about 50° C. to about 80° C., even more preferably about 50° C. to about 70° C., and most preferably about 60° C., preferably for about 16 hours.

In another embodiment, the present invention encompasses a new process for preparing anhydrous lapatinib ditosylate comprising slurrying lapatinib ditosylate in an organic solvent selected from the group consisting of methyl ethyl ether, acetone, isopropanol, n-butanol, methanol, tetrahydrofuran, ethyl acetate, dimethyl carbonate, dichloromethane, chloroform, acetonitrile, and a mixture of tetrahydrofuran/water; and drying the obtained precipitate.

Preferably, the slurry is maintained at a temperature of about 0° C. to about 50° C., more preferably about 20° C. to about 50° C., and most preferably about 20° C. to about 30° C., preferably for about an hour to about 24 hours, more preferably for about 2 hours to about 8 hours, and most preferably for about 2 hours. The precipitate is then dried at an elevated temperature, preferably under reduced pressure. For example, the precipitate can be dried at about 40° C. to about 70° C., and more preferably about 40° C.

In another embodiment, the invention encompasses a process for preparing anhydrous lapatinib ditosylate comprising forming a slurry of lapatinib base, and p-toluenesulfonic acid, in toluene; and drying the obtained precipitate.

Preferably, the slurry is maintained at a temperature of about 0° C. to about 50° C., more preferably about 20° C. to about 50° C., and most preferably about 20° C. to about 30° C., preferably for about an hour to about 24 hours, more preferably for about 2 hours to about 8 hours, and most preferably for about 2 hours.

In another embodiment, the present invention encompasses a process for preparing anhydrous lapatinib ditosylate comprising dissolving lapatinib ditosylate in an organic solvent selected from the group consisting of dimethylacetamide, dimethylformamide, and dimethylsulfoxide; and adding an anti solvent selected from the group consisting of isopropanol, acetonitrile, MTBE, acetone, tetrahydrofuran, methanol, and ethanol. The pair of solvents and antisolvents can be selected from the group consisting of: DMF/isopropanol, DMF/acetonitrile, DMF/MTBE, DMF/acetone, DMA/MTBE, DMSO/tetrahydrofuran, DMSO/acetone, DMSO/methanol, and DMSO/ethanol. When DMF/acetonitrile, DMF/acetone, and DMA/MTBE are used, the precipitate is further dried.

Preferably, the mixture is maintained at about 0° C. to about 70° C., preferably about 20° C. to about 30° C. for about 2 hours. The precipitate can be further dried. For example at about 40° C. to about 90° C., more preferably about 50° C. to about 80° C., and most preferably about 60° C., preferably, under reduced pressure.

The present invention provides a pharmaceutical formulation comprising one or more of the above described lapatinib ditosylate Forms I, II, III, IV, V, VI, VII, VIII, IX, XI, XII, XIII, XIV, XV, XVI, XVII, XVIII, or XIX. This pharmaceutical composition may additionally comprise at least one pharmaceutically acceptable excipient.

Alternatively, pharmaceutical formulations of the present invention may also contain one of the novel crystalline forms of lapatinib ditosylate disclosed herein in a mixture with other forms of lapatinib ditosylate.

In another embodiment, the invention encompasses a pharmaceutical formulation comprising one or more of the above described lapatinib ditosylate Forms I, II, III, IV, V, VI, VII, VIII, IX, XI, XII, XIII, XIV, XV, XVI, XVII, XVIII, or XIX for the treatment of patients with advanced metastatic breast cancer.

In addition to the active ingredient(s), the pharmaceutical formulations of the present invention may contain one or more excipients. Excipients may be added to the formulation for a variety of purposes.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

X-Ray Power Diffraction

X-Ray powder diffraction data was obtained by using methods known in the art using a SCINTAG powder X-Ray diffractometer model X'TRA equipped with a solid-state detector. Copper radiation of 1.5418 Å was used. A round aluminum sample holder with zero background was used. The scanning parameters included: range: 2-40 degrees two-theta; scan mode: continuous scan; step size: 0.05 deg.; and a rate of 3 deg/min. All peak positions are within ±0.2 degrees two theta.

Figure no. 32 was obtained by using methods known in the art using a Bruker X-Ray powder diffractometer model D8 advance equipped with lynxeye.

Scan range: 2-40°. Step size: 0.05°. Time per step: 5.2 seconds.

Example 1

To 0.1 gr solid lapatinib base Form X sample, 0.065 gr of p-toluenesulfonic acid was added to obtain a yellow solid. The resulting dry solid was stirred over 16 h at 25° C. The cake thus obtained, identified as Form I of lapatinib ditosylate.

Example 2

To 50 mg of crystalline anhydrous lapatinib ditosylate sample, a solvent was added and the resulting suspension was stirred and filtered. The various conditions are summarized in the following table:

| Experiment no. | solvent | amount (V) | stirring time (h) | stirring temperature (° C.) | result |
|---|---|---|---|---|---|
| 1 | DMF | 5 | 2 | 25 | II |
| 2 | NMP | 5 | 2 | 25 | V |

Example 3

To 50 mg of crystalline anhydrous lapatinib ditosylate sample, a solvent was added and a yellow solution was obtained. To the resulting solution an antisolvent was added, to obtain a yellow suspension. The resulting suspension was stirred and filtered. The various conditions are summarized in the following table:

| Experiment no. | solvent | amount (V) | antisolvent | amount (ml) | stirring time (h) | stirring temperature (° C.) | result |
|---|---|---|---|---|---|---|---|
| 3 | DMA | 30 | hexane | 1507.5 | 1 | 25 | VIII |
| 4 | DMA | 30 | Toluene | 603 | 1 | 25 | II |
| 5 | DMA | 30 | MTBE | 1206 | 1 | 25 | II |
| 6 | DMF | 10 | Toluene | 100.5 | 2 | 25 | II |
| 7 | DMF | 10 | Acetone | 100.5 | 2 | 25 | III |
| 8 | DMF | 10 | THF | 100.5 | 2 | 25 | III |
| 9 | DMF | 10 | Acetonitrile | 100.5 | 2 | 25 | IV |
| 10 | NMP | 30 | hexane | 1507.5 | 1 | 25 | V |
| 11 | NMP | 30 | IPA | 1809 | 1 | 25 | V |
| 12 | NMP | 30 | Acetone | 1206 | 1 | 25 | V |
| 13 | NMP | 30 | THF | 1206 | 1 | 25 | V |
| 14 | NMP | 30 | MTBE | 1206 | 1 | 25 | V |
| 15 | NMP | 30 | Acetonitrile | 1206 | 1 | 25 | V |
| 16 | DMF | 10 | MTBE | 100.5 | 2 | 25 | VI |

Example 4

To the mixture of 0.1 gr solid lapatinib-base Form X and 0.065 gr PTSA (p-toluenesulfonic acid), 3 ml (30V) Heptane was added to obtain yellow suspension. The resulting suspension was stirred over 18 h at 25° C. The obtained cake was analyzed and was identified as Form I. The cake thus obtained was dried 16 h, 40° C. in a vacuum oven, identified as Form VII of lapatinib ditosylate.

Example 5

To the mixture of 0.5 gr solid lapatinib-base Form X and 0.33 gr PTSA, 15 ml (30V) diethyl ether was added to obtain yellow suspension. The resulting suspension was stirred over 2 h at 25° C. The cake thus obtained was dried 16 h, 40° C. in a vacuum oven, identified as Form IX of lapatinib ditosylate.

Example 6

To the mixture of 0.5 gr solid lapatinib-base Form X and 0.33 gr PTSA, 15 ml (30V) hexane was added to obtain yellow suspension. The resulting suspension was stirred over 2 h at 25° C. The cake thus obtained was dried 16 h, 40° C. in a vacuum oven, identified as Form I of lapatinib ditosylate.

Example 7

To the mixture of 0.5 gr solid lapatinib-base Form X and 0.33 gr PTSA, 15 ml (30V) methyl tert butyl ether was added to obtain yellow suspension. The resulting suspension was stirred over 2 h at 25° C. The cake thus obtained was dried 16 h, 40° C. in a vacuum oven, identified as Form VII of lapatinib ditosylate.

Example 8

To 0.5 gr solid lapatinib-base Form X sample, 0.33 gr PTSA was added to obtain a yellow solid. The resulting solid was stirred over 66 h at 25° C. The cake thus obtained, identified by PXRD as Form I of lapatinib ditosylate.

Example 9

To 0.5 gr solid lapatinib-base Form X sample, 0.33 gr PTSA was added to obtain a yellow solid. The resulting solid was stirred over 24 h at 40° C. The cake thus obtained, identified by PXRD as Form I of lapatinib ditosylate.

Example 11

To the mixture of 0.3 gr solid lapatinib-base Form X and 0.198 gr PTSA, 9 ml (30 V) of hexane was added to obtain a yellow suspension. The resulting suspension was stirred over 24 h at 40° C., then filtered. The cake thus obtained was dried for 16 h, 40° C. in a vacuum oven and identified by PXRD as Form I of lapatinib ditosylate.

Example 12

Lapatinib ditosylate Form I was heated to 100-120° C. for 30 minutes and cooling to about 25° C. The product of the heating was identified by PXRD as Form XI of lapatinib ditosylate.

Example 13

A drop of ethanol was added to about 50 mg of lapatinib ditosylate Form I that was placed in a mortar. The powder and the ethanol were strongly ground together with a pestle for 1 minute. The product of the grinding was identified by PXRD as Form XI of lapatinib ditosylate.

Example 14

A drop of isopropanol was added to about 50 mg of lapatinib ditosylate Form I that was placed in a mortar. The powder and the isopropanol were strongly ground together with a pestle for 1 minute. The product of the grinding was identified by PXRD as Form XI of lapatinib ditosylate.

Example 15

1.14 g of lapatinib ditosylate was dissolved in 55 ml (50V) of DMSO. The solution was lyophilized at temperature of −40° C. under vacuum for 4 days. The cake thus obtained was identified as Form XI of lapatinib ditosylate.

Example 16

To the mixture of 0.5 gr solid lapatinib-base Form X and 0.33 gr PTSA, 15 ml (30V) MTBE was added to obtain a yellow suspension. The resulting suspension was stirred over 2 h at 25° C. The cake thus obtained was identified by PXRD as Form XI of lapatinib ditosylate.

Example 17

The cake obtained by the procedure described in example 14 was dried for 16 h, 40° C. in a vacuum oven and identified by PXRD as Form VII of lapatinib ditosylate.

Example 18

A drop of water was added to about 50 mg of lapatinib ditosylate Form I that was placed in a mortar. The powder and the water were strongly ground together with a pestle for 1 minute. The product of the grinding was identified by PXRD as Form XII of lapatinib ditosylate.

Example 19

To 0.5 g solid lapatinib ditosylate, 30V dimethylacetamide was added and a yellow solution was obtained. To the resulting solution 150V hexane was added, to obtain yellow suspension. The resulting suspension was stirred over 2 h at 25° C., whereupon it was filtered. The cake thus obtained was dried 16 h, 60° C. in a vacuum oven, identified as Form XIII of lapatinib-ditosylate.

Example 20

To a solid 1 g lapatinib ditosylate sample, 30V dimethylacetamide was added and a yellow solution was obtained. To the resulting solution 100V MeOH was added, to obtain a yellow suspension. The resulting suspension was stirred over 16 h at 25° C. The cake thus obtained was dried for 16 h, 60° C. in a vacuum oven, identified as Form XIV of lapatinib ditosylate.

Example 22

To a solid lapatinib-DTS sample, 12V methyl ethyl ether was added and the resulting yellow suspension was stirred over 2 h at 50° C., whereupon it was filtered. The cake thus obtained was dried 16 h, 40° C. in a vacuum oven, identified as anhydrous lapatinib-DTS.

Example 23

To a solid lapatinib-DTS sample, 12V acetone was added and the resulting yellow suspension was stirred over 2 h at 30° C., whereupon it was filtered. The cake thus obtained was dried 16 h, 40° C. in a vacuum oven, identified as anhydrous lapatinib-DTS.

Example 24

To a solid lapatinib-DTS sample, 12V isopropanol was added and the resulting yellow suspension was stirred over 2 h at 50° C., whereupon it was filtered. The cake thus obtained was dried 16 h, 40° C. in a vacuum oven, identified as anhydrous lapatinib-DTS.

Example 25

To a solid lapatinib-DTS sample, 12V n-butanol was added and the resulting yellow suspension was stirred over 2 h at 50° C., whereupon it was filtered. The cake thus obtained was dried 16 h, 40° C. in a vacuum oven, identified as anhydrous lapatinib-DTS.

Example 26

To a solid lapatinib-DTS sample, 12V methanol was added and the resulting yellow suspension was stirred over 2 h at 30° C., whereupon it was filtered. The cake thus obtained was dried 16 h, 40° C. in a vacuum oven, identified as anhydrous lapatinib-DTS.

Example 28

To a solid lapatinib-DTS sample, 12V tetrahydrofuran was added and the resulting yellow suspension was stirred over 2 h at 30° C., whereupon it was filtered. The cake thus obtained was dried 16 h, 40° C. in a vacuum oven, identified as anhydrous lapatinib-DTS.

Example 29

To a solid lapatinib-DTS sample, 12V ethyl acetate was added and the resulting yellow suspension was stirred over 2 h at 30° C., whereupon it was filtered. The cake thus obtained was dried 16 h, 40° C. in a vacuum oven, identified as anhydrous lapatinib-DTS.

Example 30

To a solid lapatinib-DTS sample, 12V dimethyl carbonate was added and the resulting yellow suspension was stirred over 2 h at 50° C., whereupon it was filtered. The cake thus obtained was dried 16 h, 40° C. in a vacuum oven, identified as anhydrous lapatinib-DTS.

Example 31

To a solid lapatinib-DTS sample, 12V dichloromethane was added and the resulting yellow suspension was stirred over 2 h at 30° C., whereupon it was filtered. The cake thus obtained was dried 16 h, 40° C. in a vacuum oven, identified as anhydrous lapatinib-DTS.

Example 32

To a solid lapatinib-DTS sample, 12V chloroform was added and the resulting yellow suspension was stirred over 2 h at 30° C., whereupon it was filtered. The cake thus obtained was dried 16 h, 40° C. in a vacuum oven, identified as anhydrous lapatinib-DTS.

Example 34

To a solid lapatinib-DTS sample, 12V acetonitrile was added and the resulting yellow suspension was stirred over 2 h at 50° C., whereupon it was filtered. The cake thus obtained was dried 16 h, 40° C. in a vacuum oven, identified as anhydrous lapatinib-DTS.

Example 35

To a solid lapatinib-DTS sample, 10V dimethylformamide was added. To the resulting solution 10V isopropanol was added, to obtain yellow suspension. The resulting suspension was stirred over 2 h at 25° C., whereupon it was filtered. The cake thus obtained identified as anhydrous lapatinib-DTS.

Example 36

To a solid lapatinib-DTS sample, 10V dimethylformamide was added. To the resulting solution 10V acetonitrile was added, to obtain yellow suspension. The resulting suspension was stirred over 2 h at 25° C., whereupon it was filtered. The cake thus obtained was dried 16 h, 60° C. in a vacuum oven, identified as anhydrous lapatinib-DTS.

Example 38

To a solid lapatinib-DTS sample, 10V dimethylformamide was added. To the resulting solution 10V acetone was added, to obtain yellow suspension. The resulting suspension was stirred over 2 h at 25° C., whereupon it was filtered. The cake thus obtained was dried 16 h, 60° C. in a vacuum oven, identified as anhydrous lapatinib-DTS.

Example 40

To a solid lapatinib-DTS sample, 30V dimethylacetamide was added. To the resulting solution 120V methyl tert butyl ether was added, to obtain yellow suspension. The resulting suspension was stirred over 1 h at 25° C., whereupon it was filtered. The cake thus obtained was dried 16 h, 60° C. in a vacuum oven, identified as anhydrous lapatinib-DTS.

Example 41

To a solid lapatinib-DTS sample, 5V dimethylsulfoxide was added. To the resulting solution 5V tetrahydrofuran was added, to obtain yellow suspension. The resulting suspension was stirred over 2 h at 25° C., whereupon it was filtered. The cake thus obtained was identified as anhydrous lapatinib-DTS.

Example 42

To a solid lapatinib-DTS sample, 5V dimethylsulfoxide was added. To the resulting solution 5V acetone was added, to obtain yellow suspension. The resulting suspension was stirred over 2 h at 25° C., whereupon it was filtered. The cake thus obtained was identified as anhydrous lapatinib-DTS.

Example 43

To a solid lapatinib-DTS sample, 5V dimethylsulfoxide was added. To the resulting solution 5V acetonitrile was added, to obtain yellow suspension. The resulting suspension was stirred over 2 h at 25° C., whereupon it was filtered. The cake thus obtained was identified as anhydrous lapatinib-DTS.

Example 44

To a solid lapatinib-DTS sample, 10V dimethylsulfoxide was added. To the resulting solution 100V methanol was added, to obtain yellow suspension. The resulting suspension was stirred over 16 h at 25° C., whereupon it was filtered. The cake thus obtained was dried 16 h, 60° C. in a vacuum oven, identified as anhydrous lapatinib-DTS.

Example 45

To a solid lapatinib-DTS sample, 10V dimethylsulfoxide was added. To the resulting solution 100V ethanol was added, to obtain yellow suspension. The resulting suspension was stirred over 16 h at 25° C., whereupon it was filtered. The cake thus obtained was dried 16 h, 60° C. in a vacuum oven, identified as anhydrous lapatinib-DTS.

Example 46

To a solid lapatinib-DTS sample, a mixture of 5/5V tetrahydrofuran/H2O was added and the resulting yellow suspension was stirred over 2 h at 30° C., whereupon it was filtered. The cake thus obtained was dried 16 h, 40° C. in a vacuum oven, identified as anhydrous lapatinib-DTS.

Example 47

To the mixture of 0.5 gr solid lapatinib-base and 0.33 gr PTSA, 15 ml (30V) Toluene was added and the resulting yellow suspension was stirred over 2 h at 25° C., whereupon it was filtered. The cake thus obtained was dried 16 h, 40° C. in a vacuum oven, identified as anhydrous lapatinib-DTS.

Example 48

To a solid lapatinib-DTS sample, 10V water was added and the resulting yellow suspension was stirred over 2 h at 50° C., whereupon it was filtered. The cake thus obtained was dried 16 h, 40° C. in a vacuum oven, identified as lapatinib-DTS monohydrate.

Example 49

To a solid lapatinib-DTS sample, a mixture of 5V water/5V acetone was added and the resulting yellow suspension was stirred over 2 h at 30° C., whereupon it was filtered. The cake thus obtained was dried 16 h, 40° C. in a vacuum oven, identified as lapatinib-DTS monohydrate.

Example 50

To a solid lapatinib-DTS sample, a mixture of 5V $H_2O$/5V methanol was added and the resulting yellow suspension was stirred over 2 h at 30° C., whereupon it was filtered. The cake thus obtained was dried 16 h, 40° C. in a vacuum oven, identified as lapatinib-DTS monohydrate.

Example 51

To a solid lapatinib-DTS sample, a mixture of 5V $H_2O$/5V ethanol was added and the resulting yellow suspension was stirred over 2 h at 30° C., whereupon it was filtered. The cake thus obtained was dried 16 h, 40° C. in a vacuum oven, identified as lapatinib-DTS monohydrate.

Example 52

To a solid lapatinib-DTS sample, a mixture of 5V $H_2O$/5V isopropanol was added and the resulting yellow suspension was stirred over 2 h at 50° C., whereupon it was filtered. The cake thus obtained was dried 16 h, 40° C. in a vacuum oven, identified as lapatinib-DTS monohydrate.

Example 53

To a solid lapatinib-DTS sample, 5V H$_2$O/5V acetonitrile was added and the resulting yellow suspension was stirred over 2 h at 50° C., whereupon it was filtered. The cake thus obtained was dried 16 h, 40° C. in a vacuum oven, identified as lapatinib-DTS monohydrate.

Example 55

To a solid lapatinib-DTS sample, 30V dimethylacetamide was added. To the resulting solution 120V THF was added, to obtain yellow suspension. The resulting suspension was stirred over 1 h at 25° C., whereupon it was filtered. The cake thus obtained was identified as lapatinib-DTS monohydrate.

Example 56

To a solid lapatinib-DTS sample, 30V dimethylacetamide was added. To the resulting solution 120V ethyl acetate was added, to obtain yellow suspension. The resulting suspension was stirred over 1 h at 25° C., whereupon it was filtered. The cake thus obtained was identified as lapatinib-DTS monohydrate.

Example 57

To a solid lapatinib-DTS sample, 30V dimethylacetamide was added. To the resulting solution 120V acetone was added, to obtain yellow suspension. The resulting suspension was stirred over 1 h at 25° C., whereupon it was filtered. The cake thus obtained was identified as lapatinib-DTS monohydrate.

Example 58

To a solid lapatinib-DTS sample, 30V dimethylacetamide was added. To the resulting solution 120V acetonitrile was added, to obtain yellow suspension. The resulting suspension was stirred over 1 h at 25° C., whereupon it was filtered. The cake thus obtained was identified as lapatinib-DTS monohydrate.

Example 59

To a solid lapatinib-DTS sample, 30V dimethylacetamide was added. To the resulting solution 90V isopropanol was added, to obtain yellow suspension. The resulting suspension was stirred over 16 h at 25° C., whereupon it was filtered. The cake thus obtained was identified as lapatinib-DTS monohydrate.

Example 61

To a solid lapatinib-DTS sample, 5V dimethylsulfoxide was added. To the resulting solution 5V IPA was added, to obtain yellow suspension. The resulting suspension was stirred over 2 h at 25° C., whereupon it was filtered. The cake thus obtained was dried 16 h, 60° C. in a vacuum oven, identified as lapatinib-DTS monohydrate.

Example 62

To the mixture of 0.5 gr solid lapatinib-base and 0.33 gr PTSA, 15 ml (30V) methanol was added and the resulting yellow suspension was stirred over 18 h at 25° C., whereupon it was filtered. The cake thus obtained was, identified as lapatinib-DTS monohydrate.

Example 63

To a solid lapatinib-DTS (0.5 gr) sample, 10V Dimethylformamide was added and yellow solution was obtained. To the resulting solution 150V heptane was added, to obtain yellow suspension. The resulting suspension was stirred over 6 h at 25° C., whereupon it was filtered. The cake thus obtained was identified as Form VI of lapatinib-DTS.

Example 64

To a solid lapatinib-DTS sample, 10V dimethylformamide was added and yellow solution was obtained. To the resulting solution 150V heptane was added, to obtain yellow suspension. The resulting suspension was stirred over 6 h at 25° C., whereupon it was filtered. The cake thus obtained was dried 16 h, 60° C. in a vacuum oven, identified as Form XIX of lapatinib-DTS.

Example 65

To a solid lapatinib-DTS sample, 20V dimethylacetamide was added and yellow solution was obtained. To the resulting solution 150V hexane was added, to obtain yellow suspension. The resulting suspension was stirred over 16 h at 25° C., whereupon it was filtered. The cake thus obtained was identified as Form VIII of lapatinib-DTS.

Example 69

To a solid lapatinib-DTS sample, 10V dimethylformamide was added and yellow solution was obtained. To the resulting solution 150V hexane was added, to obtain yellow suspension. The resulting suspension was stirred over 5 h at 25° C., whereupon it was filtered. The cake thus obtained was dried 16 h, 60° C. in a vacuum oven, identified as a mixture of Forms XIX and XIII of lapatinib-DTS.

Example 71

To 0.5 g solid lapatinib ditosylate, 30V dimethylacetamide was added and a yellow solution was obtained. To the resulting solution, 150V hexane was added to obtain a yellow suspension. The resulting suspension was stirred over 2 h at 25° C., whereupon it was filtered. The cake thus obtained was identified as Form VIII of lapatinib-DTS.

Example 73

The cake obtained at example 72 was dried for 40 h at 60° C. in a vacuum oven, identified as Form XIII of lapatinib-DTS.

Example 74

To 0.5 g of solid anhydrous lapatinib-DTS, 10V dimethylformamide was added and a yellow solution was obtained. To the resulting solution, 150V hexane was added to obtain a yellow suspension. The resulting suspension was stirred over 7 h at 25° C., whereupon it was filtered. The cake thus obtained was identified as Form VI of lapatinib-DTS.

Example 75

The cake obtained at example 74 was dried for 16 h at 60° C. in a vacuum oven, identified as a polymorphic mixture of Forms XIX and XIII of lapatinib-DTS.

Example 76

To the mixture of 0.31 gr solid lapatinib-base Form X and 0.186 gr PTSA in 30V (15 ml) dimethylacetamide, 75 ml (150V) hexane was added to obtain a yellow suspension. The resulting suspension was stirred over 5 h at 25° C. The cake thus obtained was dried for 16 h at 60° C. in a vacuum oven, identified as Form XIII of lapatinib-DTS.

Example 77

To the mixture of 1 gr solid lapatinib-base Form X and 0.6 gr PTSA, 48 ml (30V) dimethylacetamide was added to obtain a yellow solution. 120 ml (75V) hexane was added dropwise into the prepared solution over 5 h and the resulting suspension was stirred over 24 h at 25° C., then filtered. The cake thus obtained was identified as Form VIII of lapatinib-DTS.

Example 78

The cake obtained at example 77 was dried for 36 h at 60° C. in a vacuum oven, identified as Form XIII of lapatinib-DTS.

Example 79

To 5 gr of solid anhydrous lapatinib-DTS sample, 50 ml (10V) dimethylformamide was added and a yellow solution was obtained. To the resulting solution, 750 ml (150V) heptane was added to obtain a yellow suspension. The resulting suspension was stirred over 16 h at 25° C., whereupon it was filtered. The cake thus obtained was identified as Form VI of lapatinib-DTS.

Example 81

To 1.03 g solid lapatinib-base Form X suspension in 50 ml methyl isobutyl ketone, 0.63 g p-toluenesulfonic acid in 16 ml methyl isobutyl ketone solution was added, to obtain yellow-brownish suspension. The resulting suspension was stirred over 20 h at 25° C., then filtered. The cake thus obtained, identified as Form XVI of lapatinib-ditosylate.

Example 82

The cake thus obtained according to example 81 was dried for 120 h at 40° C. in a vacuum oven, identified as Form XVII of lapatinib-ditosylate.

Example 83

1.03 g solid lapatinib-base Form X suspension in 50 ml methyl isobutyl ketone was added into solution of 0.63 g p-toluenesulfonic acid in 16 ml methyl isobutyl ketone to obtain yellow-brownish suspension. The resulting suspension was stirred over 20 h at 25° C., then filtered. The cake thus obtained was dried for 120 h at 40° C. in a vacuum oven, identified as Form XVII of lapatinib-ditosylate.

Example 85

To 0.5 gr solid lapatinib-ditosylate sample 5V dimethylformamide was added and yellow suspension was obtained. To the resulting suspension 5V THF was added, to obtain yellow suspension. To resulting suspension 10V heptane was added, than it was stirred over 16 h at 25° C., whereupon it was filtered. The cake thus obtained was identified as Form XVIII of lapatinib-ditosylate

Example 86

To the mixture of 2 gr solid lapatinib-base, 1.2 gr PTSA, 15V dimethylformamide was added to obtain brownish solution. To the resulting solution 150V heptane was added, to obtain yellow suspension. The resulting suspension was stirred over 5 h at 25° C., whereupon it was filtered. The cake thus obtained was dried 48 h, 50° C. in a vacuum oven, identified as Form XV of lapatinib-DTS.

Example 87

To the mixture of 2.5 gr solid lapatinib-base, 1.64 gr PTSA, 15V dimethylformamide was added to obtain orange solution. To the resulting solution 150V heptane was added, to obtain yellow suspension. The resulting suspension was stirred over 24 h at 25° C., whereupon it was filtered. The cake thus obtained was dried 48 h, 50° C. in a vacuum oven, identified as Form XIX of lapatinib-DTS.

Example 88

To a solid lapatinib-DTS sample 5V dimethylformamide was added and yellow suspension was obtained. To the resulting suspension 10V heptane was added. The resulting suspension was stirred over 3 h at 25° C., 1 h at 5° C., whereupon it was filtered. The cake thus obtained was dried 16 h, 70° C. in a vacuum oven, identified as a mixture of Forms XV and XIII of lapatinib-DTS.

Example 89

A drop of acetone was added to about 50 mg of lapatinib ditosylate Form XV that was placed in a mortar. The powder and the acetone were strongly ground together with a pestle for 1 minute. The product of the grinding was identified by PXRD as mixture of Forms XIII and XV of lapatinib ditosylate.

Example 90

50 mg of mixture of Forms XIII and XV of lapatinib ditosylate was heated to 100° C. for 30 minutes. The product of the heating was identified by PXRD as Form XV of lapatinib ditosylate.

Example 91

PTSA was added to a solution of lapatinib-base in 5V dimethylformamide, 8.03 gr (2 eq) to obtain a brownish solution.

The solution was seeded with Form VI at 40° C., than it was stirred over 1 hour, to obtain a yellow suspension. Then, it was cooled to 0° C. over 6 hours, and stirred over 10 hours. The resulting suspension was deep-cooled to −10° C. over 2 hours, and stirred over 2 hours. The obtained cake was filtered and identified as Form VI of lapatinib-DTS.

Example 92

Lapatinib ditosylate Form XIII (150 mg) were stored under DMF vapors at room temperature for 48 hours. It was then analyzed by PXRD and identified as Form XVIII of lapatinib ditosylate. After 6 hours at ambient conditions the material was retested and identified as Form XIII of lapatinib ditosylate.

Example 93

Lapatinib ditosylate Form XV (150 mg) was stored under acetone vapors at 25° C. for 48 hours. It was then analyzed by PXRD and identified as Form XIII of lapatinib ditosylate.

What is claimed is:

1. A crystalline form of lapatinib ditosylate (Form XIII) characterized by data selected from the group consisting of a PXRD pattern having peaks at about 5.9, 6.8, and 8.9±0.2 degrees 2-theta, and at least two peaks from the following list: 12.2, 13.5, 16.0, 18.7 and 22.9±0.2 degrees 2-theta; a PXRD pattern having peaks at about 5.9, 6.8, 8.9, 12.2 and 13.6±0.2 degrees 2-theta; a PXRD pattern having peaks at about 5.9, 6.8, 8.9, 12.2, 13.6, 14.6, 16.0, 19.0, 20.4 and 22.9±0.2 degrees 2-theta; a solid-state $^{13}$C NMR spectrum having signals at about 125.1, 129.6 and 150.7±0.2 ppm; and a solid-state $^{13}$C NMR spectrum having chemical shifts differences between the signal exhibiting the lowest chemical shift and another in the chemical shift range of 100 to 180 ppm of about 17.2, 21.7 and 42.8±0.1 ppm, wherein the signal exhibiting the lowest chemical shift in the chemical shift area of 100 to 180 ppm is typically at about 107.9±1 ppm.

2. The crystalline form of lapatinib ditosylate of claim 1, characterized by a PXRD pattern having peaks at about 5.9, 6.8, 8.9, 12.2 and 13.6±0.2 degrees 2-theta or a PXRD pattern having peaks at about 5.9, 6.8, 8.9, 12.2, 13.6, 14.6, 16.0, 19.0, 20.4 and 22.9±0.2 degrees 2-theta.

3. The crystalline form of lapatinib ditosylate of claim 1 having an X-ray diffraction diagram substantially as depicted in FIG. 23.

4. A process for preparing the crystalline lapatinib ditosylate of claim 1 comprising forming a solution of lapatinib ditosylate in dimethylacetamide; adding an antisolvent; and drying the obtained precipitate.

5. The process of claim 4 wherein the antisolvent is hexane.

6. The process of claim 4, wherein the lapatinib ditosylate is prepared in situ by a process comprising combining lapatinib base and p-toluenesulfonic acid in dimethylacetamide.

7. A pharmaceutical composition comprising the crystalline lapatinib ditosylate of claim 1.

* * * * *